(12) United States Patent
Moran

(10) Patent No.: US 7,727,519 B2
(45) Date of Patent: Jun. 1, 2010

(54) METHOD FOR TREATING HEPATITIS C VIRUS WITH OMEGA INTERFERON

(75) Inventor: Mark Stanford Moran, Orinda, CA (US)

(73) Assignee: Intarcia Therapeutics, Inc., Hayward, CA (US)

(*) Notice: Subject to any disclaimer, the term of this patent is extended or adjusted under 35 U.S.C. 154(b) by 713 days.

(21) Appl. No.: 10/982,532

(22) Filed: Nov. 5, 2004

(65) Prior Publication Data

US 2005/0201980 A1 Sep. 15, 2005

Related U.S. Application Data

(63) Continuation of application No. 10/004,118, filed on Oct. 30, 2001.

(60) Provisional application No. 60/245,883, filed on Nov. 3, 2000.

(51) Int. Cl.
*A61K 38/21* (2006.01)
*C07K 14/00* (2006.01)

(52) U.S. Cl. ............... 424/85.4; 424/85.7; 530/351

(58) Field of Classification Search ............... None
See application file for complete search history.

(56) References Cited

U.S. PATENT DOCUMENTS

| | | | |
|---|---|---|---|
| 4,211,771 A | 7/1980 | Witkowski et al. | |
| 4,673,405 A | 6/1987 | Guittard et al. | |
| 4,675,184 A | 6/1987 | Hasegawa et al. | |
| 4,695,623 A | 9/1987 | Stabinsky | |
| 4,727,138 A | 2/1988 | Goeddel et al. | |
| 4,762,791 A | 8/1988 | Goeddel et al. | |
| 4,820,638 A | 4/1989 | Swetly et al. | |
| 4,845,196 A | 7/1989 | Cowling | |
| 4,847,079 A | 7/1989 | Kwan | |
| 4,885,166 A | 12/1989 | Meyer et al. | |
| 4,897,471 A | 1/1990 | Stabinsky | |
| 4,915,954 A | 4/1990 | Ayer et al. | |
| 4,917,887 A | 4/1990 | Hauptmann et al. | |
| 4,917,895 A | 4/1990 | Lee et al. | |
| 4,929,554 A | 5/1990 | Goeddel et al. | |
| 4,976,966 A * | 12/1990 | Theeuwes et al. ........ | 424/473 |
| 5,004,689 A | 4/1991 | Fiers et al. | |
| 5,019,382 A | 5/1991 | Cummins, Jr. | |
| 5,112,614 A | 5/1992 | Magruder et al. | |
| 5,120,306 A | 6/1992 | Gosselin | |
| 5,120,832 A * | 6/1992 | Goeddel et al. ........ | 530/351 |
| 5,207,752 A | 5/1993 | Sorensen et al. | |
| 5,221,278 A | 6/1993 | Linkwitz et al. | |
| 5,231,176 A | 7/1993 | Goeddel et al. | |
| 5,318,558 A | 6/1994 | Linkwitz et al. | |
| 5,324,280 A | 6/1994 | Wong et al. | |
| 5,368,863 A | 11/1994 | Eckenhoff et al. | |
| 5,413,572 A | 5/1995 | Wong et al. | |
| 5,429,602 A | 7/1995 | Hauser | |
| 5,443,459 A | 8/1995 | Wong et al. | |
| 5,529,914 A | 6/1996 | Hubbell et al. | |
| 5,543,156 A | 8/1996 | Roorda et al. | |
| 5,574,137 A | 11/1996 | Gray et al. | |
| 5,602,010 A | 2/1997 | Hauptmann et al. | |
| 5,605,688 A | 2/1997 | Himmler et al. | |
| 5,660,847 A | 8/1997 | Magruder et al. | |
| 5,676,942 A | 10/1997 | Testa et al. | |
| 5,690,925 A | 11/1997 | Gray et al. | |
| 5,728,396 A | 3/1998 | Peery et al. | |
| 5,738,845 A | 4/1998 | Imakawa | |
| 5,795,779 A | 8/1998 | McCormick et al. | |
| 5,807,876 A | 9/1998 | Armistead et al. | |
| 5,858,746 A | 1/1999 | Hubbell et al. | |
| 5,906,816 A | 5/1999 | Soos et al. | |
| 5,908,621 A | 6/1999 | Glue et al. | |
| 5,939,286 A | 8/1999 | Johnson et al. | |
| 5,942,223 A | 8/1999 | Bazer et al. | |
| 5,985,305 A | 11/1999 | Peery et al. | |
| 6,007,805 A | 12/1999 | Foster et al. | |

(Continued)

FOREIGN PATENT DOCUMENTS

EP 0 079 405 A1 5/1983

(Continued)

OTHER PUBLICATIONS

Zhang et al. Efficacy observations of different dosages of interferon to treat 150 Hepatitis B carriers. Current Physician. 1997. vol. 2, No. 12, pp. 45-46.*

(Continued)

*Primary Examiner*—Robert Landsman
*Assistant Examiner*—Bruce D Hissong
(74) *Attorney, Agent, or Firm*—Gary R. Fabian; Barbara G. McClung

(57) ABSTRACT

Methods for the treatment of interferon-response disorders by administration of an interferon alone or in combination with adjunctive therapy are described. The invention encompasses providing to a patient both a formulation of an interferon that is suitable for short-term administration and a formulation of an interferon associated with a sustained release delivery system that is suitable for long-term administration. A principal advantage of the method is that responsiveness to treatment can be ascertained with short-term dosimetric techniques using one formulation of an interferon, which permits the appropriate selection of a dose that is both effective and safe for long-term administration using the second formulation.

22 Claims, 5 Drawing Sheets

U.S. PATENT DOCUMENTS

| | | | |
|---|---|---|---|
| 6,060,450 | A | 5/2000 | Soos et al. |
| 6,069,133 | A | 5/2000 | Carlo et al. |
| 6,113,938 | A | 9/2000 | Chen et al. |
| 6,129,761 | A | 10/2000 | Hubbell |
| 6,172,046 | B1 | 1/2001 | Albrecht |
| 6,204,022 | B1 | 3/2001 | Johnson et al. |
| 6,372,218 | B1 | 4/2002 | Cummins, Jr. |
| 6,436,091 | B1 | 8/2002 | Harper et al. |
| 6,472,512 | B1 | 10/2002 | LaFleur et al. |
| 6,833,256 | B1 | 12/2004 | Pontzer et al. |
| 6,875,748 | B2 | 4/2005 | Manthorpe et al. |
| 7,101,567 | B1 | 9/2006 | Sano et al. |
| 2004/0225113 | A1 | 11/2004 | LaFleur et al. |

FOREIGN PATENT DOCUMENTS

| | | |
|---|---|---|
| EP | 1 046 399 | 10/2000 |
| EP | 1 084 703 | 3/2001 |
| WO | WO 93/08832 A1 | 5/1993 |
| WO | WO 96/03116 | 2/1996 |
| WO | WO 99/62501 | 12/1999 |
| WO | WO 00/38652 | 7/2000 |
| WO | WO 00/39280 A2 | 7/2000 |
| WO | WO 00/39280 A3 | 7/2000 |
| WO | WO 00/40273 A2 | 7/2000 |
| WO | WO 00/40273 A2 | 7/2000 |
| WO | WO 00/40273 A3 | 7/2000 |
| WO | WO 00/40273 A3 | 7/2000 |
| WO | WO 02/36072 | 5/2002 |
| WO | WO 03/030923 A1 | 4/2003 |

OTHER PUBLICATIONS

Adolf, G., et al., "Antigenic structure of human interferon ω1 (Interferon αII1): comparison with other human interferons," *J. Gen. Virol.* 68(Pt 6):1669-1676 (Jun. 1987).

Adolf, G. et al. "Monoclonal antibodies and enzyme immunoassays specific for human interferon (IFN) ω1: evidence that IFN- ω1 is a component of human leukocyte IFN," *Virology* 175(2):410-471 (Apr. 1990).

Adolf, G., et al., "Purification and characterization of natural human interferon ω1," *J. Bio. Chem.* 265(16):9290-9295 (Jun. 1990).

Adolf. G., et al., "Human interferon ω1: isolation of the gene, expression in Chinese hamster ovary cells and characterization of the recombinant protein," *Biochim. Biophys. Acta* 108(9):167-174 (Jun. 1991).

Aulitzky, W., "Acute hematologic effects of interferon α, interferon γ, tumor necrosis factor α and Interleukin 2," *Ann. Hemetol.* 62(1):25-31 (Feb. 1991).

Balkwill, F. "Interferons," in *Cytokines in Cancer Therapy*, Oxford University Press: Oxford, GB (1989).

Balkwill, F., "Interferons," *Lancet* 1(8646):1060-1063 (May 1989).

Bekkering, F., et al., "Estimation of early hepatitis C viral clearance in patients receiving daily interferon and ribavirin therapy using a mathematical model," *Hepatology* 33(2):419-423 (Feb. 2001).

Bolinger, A., et al., "Recombinant interferon γ for treatment of chronic granulomatous disease and other disorders," *Clin. Pharm.* 11(10):834-850 (Oct. 1992).

Bonkovsky, H., et al., "Outcomes research in chronic viral hepatitis C: effects of interferon therapy," *Can. J. Gastroenterol.* 14(Supp. B):21B-29B (Jul.-Aug. 2000).

Borden, E., et al., "Second-generation interferons for cancer: clinical targets," *Semin. Cancer Biol.* 10(2):125-144 (Apr. 2000).

Condino-Neto, A., "Interferon-γ improves splicing efficiency of CYBB gene transcripts in an interferon responsive variant of chronic granulomatous disease due to a splice site consensus region mutation," *Blood* 95(11):3548-3554 (Jun. 2000).

Davis, G., et al., "Durability of viral response to interferon alone or in combination with oral ribavirin in patients with chronic hepatitis C," *Prog. Abstr. 50th Annu. Mtg. Postgrad. Courses Am. Assn. Study Liver Dis.*, Dallas, TX, Abstract 570 (Nov. 5-9, 1999).

Di Marco, V., et al., "Combined treatment of relapse of chronic hepatitis C with high-dose α-2B interferon plus ribavirin for 6 or 12 months," *Prog. Abstr. 50th Annu. Mtg. Postgrad. Courses Am. Assn. Study Liver Dis.*, Dallas, TX, Abstract 569 (Nov. 5-9, 1999).

Elias, L., et al., "Infusional Interleukin-2 and 5-fluorouracil with subcutaneous interferon-α for the treatment of patients with advanced renal cell carcinoma: a southwest oncology group Phase II study," Cancer 89(3):597-603 (Aug. 2000).

Fang, J., et al., "The impact of baseline liver histology on virologic response to interferon α-2b±ρ ribavirin therapy in patients with chronic hepatitis C," *Prog. Abstr. 50th Annu. Mtg. Postgrad. Courses Am. Assn. Study Liver Dis.*, Dallas, TX, Abstract 572 (Nov. 5-9, 1999).

Ferenci, P., et al, "Combination of interferon (IFN) induction therapy and ribavirin in chronic hepatitis C," *Prog. Abstr. Dig. Dis. Week 2000*, San Diego, CA, Abstract 977 (May 21-24, 2000).

Fontaine, H., et al., "Recovery from chronic hepatitis C in long-term responders to ribarivin plus interferon α," *Lancet* 356(9223):41 (Jul. 2000).

Glue, P., et al., "A dose-ranging study of Peg-intron and ribavirin in chronic hepatitis C—safety, efficacy, and virological rationale," *Prog. Abstr. 50th Annu. Mtg. Postgrad. Courses Am. Assn. Study Liver Dis.*, Dallas, TX, Abstract 571 (Nov. 5-9, 1999).

Gonzales, H., et al., "Randomized controlled trial including an initial 4-week 'induction' period during one year of high-dose interferon α-2B treatment for chronic hepatitis C," *Prog. Abstr. Dig. Dis. Week 2000*, San Diego, CA, Abstract 975 (May 21-24, 2000).

Grant, P. et al., "Combination therapy with interferon-α plus N-acetyl cystein for chronic hepatitis C: a placebo controlled double-blind multicentre study," *J. Med. Virol.* 61(4):439-442 (Aug. 2000).

Heim, M., et al., "Intracellular signaling and antiviral effects of interferons," *Dig. Liver Dis.* 32(3):257-263 (Apr. 2000).

Hellstrand, K., et al., "Histamine and cytokine therapy," *Acta Oncol.* 37(4):347-353 (1998).

Hellstrand, K., et al., "Histamine and the response to IFN-α in chronic hepatitis C," *Interferon Cytokine Res.* 18(1):21-22 (Jan. 1998).

Hellstrand, K., et al., "Histamine in immunotherapy of advanced melanoma: a pilot study," *Cancer Immunol Immunother.* 39(6):416-419 (Dec. 1994).

IFNB Multiple Sclerosis Study Group, "Interferonβ-1b is effective in relapsing-remitting multiple sclerosis," *Neurology* 43(4):655-667 (Apr. 1993).

Isaacs, A., et al., "Virus interference. I. The interferon," *Pro. R. Soc. Lond. B. Biol. Sci.* 147:258-267 (1957).

Johnson, H., et al., "How interferons fight disease," *Sci. Am.* 270(5):68-75 (May 1994).

Khalili, M., et al., "Interferon and ribavirin versus interferon and amantadine in interferon nonresponders with chronic hepatitis C," *Am. J. Gastroenterol.* 95(5):1284-1289 (May 2000).

Kita, Y., et al., "Characterization of a polyethylene glycol conjugate of recombinant human interferon-γ," *Drug Des. Deliv.* 6(3):157-167 (Sep. 1990).

Knobler, R., et al., "Systemic α-interferon therapy of multiple sclerosis," *Neurology* 34(10):1273-1279 (Oct. 1984).

Kovacevic, Z., et al., "Treatment of chronic viral hepatitis B in secondary membranoproliferative glomerulonephritis using recombinant α-2 interferon," *Maksic Dj Vojnosanit. Pregl.* 57(2):235-240 (Mar.-Apr. 2000).

Kracke, A., et al., "Mx proteins in blood leukocytes for monitoring interferon β-1b therapy in patients with MS," *Neurology* 54(1):193-199 (Jan. 2000).

Kronenberger, B., et al., "Influence of interferon-α on CD82-expression in HCV-positive patients," *Prog. Abstr. Dig. Dis. Week 2000*, San Diego, CA, Abstract 976 (May 21-24, 2000).

Krown, S., et al., "Interferons and interferon inducers in cancer treatment," *Semin. Oncol.* 13(2):207-217 (1986).

Kunzi, M., et al., "Role of interferon-stimulated gene ISG-15 in the interferon-ω-mediated inhibition of human immunodeficiency virus replication," *J. Interferon Cytokine Res.* 16(11):919-927 (Nov. 1996).

Lee, J., et al., "Dynamics of hepatitis C virus quasispecies turnover during interferon-A treatment," *Prog. Abstr. Dig. Dis. Week 2000*, San Diego, CA, Abstract 974 (May 21-24, 2000).

Lukaszewski, R., et al., "Pegylated α interferon is an effective treatment for virulent Venezuelan equine encephalitis virus and has profound effects on host immune response to infection," *J. Virol.* 74(11):5006-5015 (Jun. 2000).

McHutchison, J., et al., "Interferon α-2b alone or in combination with ribavirin as initial treatment for chronic hepatitis C," *N. Engl. J. Med.* 339(21):1485-1492 (Nov. 1998).

Merad, M., et al., "Generation of monocyte-derived dendritic cells from patients with renal cell cancer: modulation of their functional properties after therapy with biological response modifiers (IFN-α plus IL-2 and IL-12)," *J. Immunother.* 23(3):369-378 (May-Jun. 2000).

Milella, M., et al., "Neutralizing antibodies to recombinant α-interferon and response to therapy in chronic hepatitis C infection," *Liver* 13(3):146-150 (Jun. 1993).

Neumann, A., et al., "Hepatitis C viral dynamics in vivo and the antiviral efficacy of interferon-α therapy," *Science* 282(5396):103-107 (Dec. 1998).

Nieforth, K., et al., "Use of an indirect pharmacodynamic stimulation model of MX protein induction to compare in vivo activity of interferon-α-2a and a polyethylene glycol-modified derivative in healthy subjects," *Clin. Pharmacol. Ther.* 59(6):636-646 (Jun. 1996).

Olaso, V., et al., "Early prediction of lack of response to treatment with interferon and interferon plus ribavirin using biochemical and virological criteria in patients with chronic hepatitis C," *Esp. Quimioter.* 12(3):220-228 (Sep. 1999).

Palmeri, S., et al., "5-Fluorouracil and recombinant α-interferon-2a in the treatment of advanced colorectal carcinoma: a dose optimization study," *J. Chemother.* 2(5):327-330 (Oct. 1990).

Panitch, H., "Interferons in multiple sclerosis," *Drugs* 44(6):946-962 (Dec. 1992).

Pimstone, N., et al., "High dose (780 MIU/52 weeks) interferon monotherapy is highly effective treatment for hepatitis C," *Prog. Abstr. Dig. Dis. Week 2000*, San Diego, CA, Abstract 973 (May 21-24, 2000).

Poynard, T., et al., "Is an 'a la carte' combined interferon α 2b plus ribavirin possible for the first line treatment in patients with chronic hepatitis C," *Hepatology* 31(1):211-218 (Jan. 2000).

Poynard, T., et al., "Randomized trial of interferon α 2b plus ribavirin for 48 weeks or for 24 weeks versus interferon α 2b plus placebo for 48 weeks for the treatment of chronic infection with hepatitis C virus," *Lancet* 352(9138):1426-1432 (Oct. 1998).

Quesada, J., et al., *Interferons in Hematological Malignancies*, S. Baron et al. (eds.), the University of Texas Press: Austin, TX, pp. 487-495 (1987).

Sen, G., et al., "The interferon system: a bird's eye view of its biochemistry," *J. Biol. Chem.* 267(8):5017-5020 (Mar. 1992).

Shiffman, M., et al., "A decline in HCV-RNA level during interferon or ihterferon/ribavirin therapy in patients with virologic nonresponse is associated with an improvement in hepatic histology," *Prog. Abstr. $50_{th}$ Annu. Mtg. Postgrad. Courses Am. Assn. Study Liver Dis.*, Dallas, TX, Abstract 567 (Nov. 5-9, 1999).

Shima, T., et al., "Serum total bile acid level as a sensitive indicator of hepatic histological improvement in chronic hepatitis C patients responding to interferon treatment," *J. Gastroenterol. Hepatol.* 15(3):294-299 (Mar. 2000).

Shiratori, Y., et al., "Histologic improvement of fibrosis in patients with hepatitis C who have sustained response to interferon therapy," *Ann. Int. Med.* 132(7):517-524 (Apr. 2000).

Simon, J., et al., "A longitudinal study of T1 hypointense lesions in relapsing MS: MSCRG trial of interferon β1a," *Neurology* 55(2):185-192 (Jul. 2000).

Sulkowski, M., et al., "Peginterferon-α-2a (40kD) and ribavirin in patients with chronic hepatitis C: a phase II open label study," *Biodrugs* 16(2):105-109 (2002).

Tanaka, H., et al., "Effect of interferon therapy on the incidence of hepatocellular carcinoma and mortality of patients with chronic hepatitis C: a retrospective cohort study of 738 patients," *Int. J. Cancer* 87(5):741-749 (Sep. 2000).

Tong, M., et al., "Prediction of response during interferon α 2b therapy in chronic hepatitis C patients using viral and biochemical characteristics: a comparison," *Hepatology* 26(6):1640-1645 (Dec. 1997).

Touza Rey, F., et al., "The clinical response to interferon-γ in a patient with chronic granulomatous disease and brain abscesses due to *Aspergillus fumigatus*," *Ann. Med. Int.* 17(2):86-87 (Feb. 2000).

Weinstock-Guttman, B., et al., "What is new in the treatment of multiple sclerosis?" *Drugs* 59(3):401-410 (Mar. 2000).

Weissmann, C., et al., "The interferon genes," *Prog. Nucleic Acid Res. Mol. Biol.* 33:251-300 (1986).

Wright, H., et al., "Preliminary experience with α-2b-interferon therapy of viral hepatitis in liver allograft recipients," *Transplantation* 53(1):121-124 (Jan. 1992).

Younossi, Z., et al., "The role of amantadine, rimantadine, ursodeoxycholic acid, and NSAIDs, alone or in combination with α interferons, in the treatment of chronic hepatitis C," *Semin. Liver Dis.* 19(Supp. 1):95-102 (1999).

Zeidner, N. S., et al., "Treatment of FeLV-induced immunodeficiency syndrome (feLV-FAIDS) with controlled release capsular implantation of 2',3'-dideoxycytidine," *Antivir. Res.* 11(3):147-160 (Apr. 1989).

Zein, N., "Interferons in the management of viral hepatitis," *Cytokines Cell Mol. Ther.* 4(4):229-241 (Dec. 1998).

Zeuzem, S., et al., "Hepatitis C virus dynamics in vivo: effect of ribavirin and interferon α on viral turnover," *Hepatology* 28(1):245-252 (Jul. 1998).

Ziesche, R., et al., "A preliminary study of long-term treatment with interferon γ-1b and low-dose prednisolone in patients with idiopathic pulmonary fibrosis," *New Engl. J. Med.* 341(17):1264-1269 (Oct. 1999).

Zheng et al. "Therapeutic Effect of Interferon Varied Dose in Treating Virus Encephalitis" Beijing Medical Journal 13(2):80-81 (1998).

Zheng et al. "Therapeutic Effect of Interferon Varied Dose in Treating Virus Encephalitis" Beijing Medical Journal 13(2):80-81 (1998).

Zhang et al. "Report on Large Dosage Interferon to Treat 30 Cases of Viral Encephalitis" Journal of Clinical Pediatrics 14(2):83-84 (1996).

Zhang et al. "Report on Large Dosage Interferon to Treat 30 Cases of Viral Encephalitis" Journal of Clinical Pediatrics 14(2):83-84 (1996).

Adamson et al., "Phase I trial and pharmacokinetic study of all-*trans*-retinoic acid administered on an intermittent schedule in combination with interferon-alpha2a in pediatric patients with refractory cancer" J Clin Oncol Nov. 1997; 15(11):3330-3337.

Bailon et al., "Rational Design of a Potent, Long-lasting Form of Interferon: A 40 kDa Branched Polyethylene Glycol-conjugated Interferon Alpha-2a for the Treatment of Hepatitis C" Bioconjugate Chemistry (2001), 12(2):195-202.

Dorr et al., "Phase I-II trial of interferon-alpha 2b by continuous subcutaneous infusion over 28 days" J Interferon Res (1988); 8:717-725.

Franchetti et al., "Furanfurin and Thiophenfurin: Two Novel TiazofurinAnalogues. Synthesis, Structure, Antitumor Activity, and Interactions with Inosine Monophosphate Dehydrogenase" Journal of Medicinal Chemistry (1995); 38(19):3829-3837.

Gause et al., "Phase I study of subcutaneously administered interleukin-2 in combination with interferon alfa-2a in patients with advanced cancer" J Clin Oncol Aug. 1996; 14(8):2234-2241.

Gosland et al., "A phase I trial of 5-day continuous infusion cisplatin and interferon alpha" Cancer Chemother Pharmacol (1995); 37(1-2):39-46.

Heathcote et al., "Peginterferon alfa-2a in Patients With Chronic Hepatitis C and Cirrhosis" New England Journal of Medicine (2000); 343(23):1673-1680.

Horton et al., "Antitumor effects of interferon-omega: in vivo therapy of human tumor xenografts in nude mice" Cancer Res 59(16):4064-4068 (Aug. 1999).

Hubel et al., "A phase I/II study of idarubicin, dexamethasone and interferon-alpha (1-Dexa) in patients with relapsed or refractory multiple myeloma" Leukemia Dec. 1997; 11 Suppl 5:S47-S51.

Iacobelli et al., "A phase I study of recombinant interferon-alpha administered as a seven-day continuous venous infusion at circadian-rhythm modulated rate in patients with cancer" Am J Clin Oncol (1995); 18(1):27-31.

Ishiwata et al., "Clinical effects of the recombinant feline interferon-omega on experimental parvovirus infection in beagle dogs" (1998); J Vet Med Sci 60(8):911-917.

Kirkwood et al., "Interferon alfa-2b adjuvant therapy of high-risk resected cutaneous melanoma: The Eastern Cooperative Oncology Group Trial EST 1684"J Clin Oncol (1996); 14(1):7-17.

Motzer et al., "Phase I trial of 40-kd branched pegylated interferon alfa-2a for patients with advanced renal cell carcinoma" Journal of Clinical Oncology (2001); 19(5):1312-1319.

Neumann et al., "Hepatitis C Viral Dynamics In Vivo and the Antiviral Efficacy of Interferon-alpha Therapy" Science 282 (1998): 103-107.

Rajkumar et al., "Phase I evaluation of radiation combined with recombinant interferon alpha-2a and BCNU for patients with high-grade glioma" Int J Radiat Oncol Biol Phys Jan. 15, 1998; 40(2):297-302.

Roth et al., "High Dose Etretinate and Interferon-alpha—A Phase I Study in Squamous Cell Carcinomas and Transitional Cell Carcinomas" Acta Oncol (1999); 38(5):613-617.

Sulkowski et al., "Pegylated Interferon Alfa-2A (Pegasys™) and Ribavirin Combination Therapy for Chronic Hepatitis C: A Phase II Open-Label Study" Gastroenterology (2000); 118(4_Suppl_2), Abstract 236.

Talpaz et al., "Phase I study of polyethylene glycol formulation of interferon alpha-2B (Schering 54031) in Philadelphia chromosome-positive chronic myelogenous leukemia" Blood (2001); 98(6):1708-1713.

Trudeau et al., "A phase I study of recombinant human interferon alpha-2b combined with 5-fluorouracil and cisplatin in patients with advanced cancer" Cancer Chemother Pharmacol (1995); 35(6):496-500.

Vokes et al., "A phase I trial of concomitant chemoradiotherapy with cisplatin dose intensification and granulocyte-colony stimulating factor support for advanced malignancies of the chest" Cancer Chemother Pharmacol (1995); 35(4):304-312.

Zeuzem et al., "Peginterferon Alfa-2a in Patients with Chronic Hepatitis C" New England Journal of Medicine (2000), 343(23):1666-1672.

InterMune® Inc. Infergen® (Interferon alfacon-1). 2002.

Hoffmann-La Roche Inc. Pegasys® (peginterferon alfa-2a). 2002.

Roche Pharmaceuticals. Roferon®-A (Interferon alfa-2a, recombinant). 2003.

Schering Corporation. Intron® A for Injection. 2001.

Schering Corporation. PEG-Intron™ (Peginterferon alfa-2b). Powder for Injection. 2003.

Buckwold V.E, et. al. "Antiviral activity of CHO-SS cell-derived human omega interferon and other human interferons against HCV RNA replicons and related viruses." Antiviral Res. Feb. 2007;73(2):118-25. Epub Sep. 11, 2006.

"AGA abstracts M1143-M1741," Gastroenterology, vol. 122, Apr. 1, 2002, pp. A278-A347, XP022329236, Abstract M1454: Open-label rising-dose study of omega interferon in IFN-naive patients with chronic hepatitis C.

Adolf, G.R., et al., "Human interferon-ω1: isolation of the gene, expression in Chinese hamster ovary cells and characterization of the recombinant protein," Biochimica et Biophysics Acta, 1089 (1991) 167-174.

Aulitzky, W., et al.,"Successful treatment of metastatic renal cell carcinoma with a biologically active dose of recombinant interferon-gamma," Journal of Clinical Oncology, vol. 7, No. 12, 1989, pp. 1875-1884, XP009079027.

Boué, O., et al., "Antiviral and antiluteolytic activity of recombinant bovine IFN-ω1 obtained from Pichia pastoris," Journal of Interferon and Cytokine Research 20:677-683 (2000).

Gan To Kagaku Ryoho, "Phase II study of recombinant leukocyte A interferon (Ro22-8181) in malignant brain tumors," Cancer & Chemotherapy, vol. 12, No. 4, Apr. 1985, pp. 913-920. Abstract Only.

Gappa, M., et al., "Juvenile laryngeal papillomatosis—a case report," Pneumologie, vol. 45, No. 11, Nov. 1991, pp. 936-938, XP009079028. Abstract Only.

Ishiwata, K., et al., "Clinical effects of the recombinant feline inter-feron-ω on experimental parvovirus infection in beagle dogs," J. Vet. Med. Sci. 60(8): 911-917.

Kubes, M., et al., "Cross-species antiviral and antiproliferative activity of human interferon-ω," Journal of Interferon Research, 14:57-59 (1994).

Künzi, M.S., et al., "Role of interferon-stimulated gene ISG-15 in the interferon-ω-mediated inhibition of human immunodeficiency virus replication," Journal of Interferon and Cytokine Research, 16:919-927 (1996).

Lee, W.M., "Therapy of hepatits C: interferon alfa-2A trials," Hepatology, vol. 26, Sep. 1997, pp. 89S-95S, XP000981288.

Marincola, F.M., et al., "Combination 1-20 therapy with interferon alfa-2a and interleukin-2 for the treatment of metastatic cancer," Journal of Clinical Oncology, vol. 13, No. 5, 1995, pp. 1110-1122, XP009078965.

McHutchison, J.G., et al., "Open-label phase 1B study of hepatitis C viral dynamics with omega interferon treatment," Hepatology, vol. 34, No. 4, Oct. 1, 2001, p. A333, XP004716177. Abstract Only.

Plauth, M., et al, "Open-label phase II study of omega interferon in previously untreated HCV infected patients," Hepatology, vol. 34, No. 4, Oct. 1, 2001, p. A331, XP004716169. Abstract Only.

Plauth, M., et al, "Open-label study of omega interferon in previously untreated HCV-infected patients," Journal of Hepatology, vol. 36, No. Supplement 1, Apr. 2002, p. 125, XP002511882. Abstract Only.

Supplementary Partial European Search Report in European Patent Application No. EP 01 99 2550 (based on PCT/US01/46137), which corresponds to U.S. Appl. No. 10/004,118.

* cited by examiner

METHOD FOR TREATING HEPATITIS C VIRUS WITH OMEGA INTERFERON

CROSS-REFERENCE

This application is a continuation of U.S. patent Ser. No. 10/004,118, filed Oct. 30, 2001, which claims benefit under 35 U.S.C. §119(e) of U.S. provisional application 60/245,883 filed Nov. 3, 2000. These applications are incorporated herein in their entirety.

FIELD OF THE INVENTION

This invention relates to a method and a kit for treating disorders, especially interferon-responsive disorders in warm-blooded animals and a method for individualizing doses of a drug, e.g. an interferon, in treating such disorders. It further relates to a method for preparing a long-term dosage for treating such disorders.

BACKGROUND OF THE INVENTION

Introduction

Long-term delivery of drugs using a device that provides a constant delivery of a drug over time has significant advantages over delivery of a drug by regular injections or even oral delivery. One advantage is that the patient may avoid "peak-related" adverse effects. Another advantage is that the patient may avoid "trough-related" ineffective therapy. Another advantage is avoiding frequent and sometimes painful injections for drugs that can't be administered orally. However, one disadvantage of long-term, constant-rate delivery of drugs is that there has not been an easy way to adjust doses for an individual patient in a given population of patients having a disease. For example, in populations with hepatitis C, individual patients will require different dosage levels of drug for treatment depending on viral load, patient age and size, etc. The use of interferons is illustrative.

Interferons

The interferons are a group of endogenous proteins produced in response to a number of infectious, proliferative or immunological disorders. Endogenous interferons have antiviral, immunomodulatory, or antiproliferative activities. The alpha and beta interferons are known as type I interferons because these molecules appear to bind to a common receptor, the so-called α-β receptor. Exogenous interferons, such as recombinant alpha (of various subtypes) or recombinant consensus interferon, have been demonstrated to be useful in the treatment of, for example, viral hepatitis C and certain cancers. A small percentage of patients who are treated with alpha or consensus interferon for periods of several months may no longer manifest positive blood tests for hepatitis C viral ribonucleic acid (HCV-RNA). Such treatment may involve only monotherapy with the interferon, or the interferon may be combined with another adjunctive therapeutic agent. Certain cancers also may stabilize or shrink in size with interferon monotherapy or with combination treatments. Exogenous beta interferon (of various subtypes) has been shown to be useful as monotherapy in the treatment of multiple sclerosis. Exogenous gamma interferon has been shown to be useful as monotherapy in the treatment of chronic granulomatous disease and more recently has been suggested to be useful in the treatment of certain pulmonary disorders. Certain interferons have been chemically modified by the addition of polyethylene glycol or polyethylene oxide polymers (pegylated interferon) and may have enhanced antiviral activity in viva as a result. Other forms of interferon-like peptides have been created using techniques to modify genes.

Adjunctive Therapeutic Agents

Ribavirin is a small organic molecule which, among other activities is known to inhibit inosine monophosphate dehydrogenase, has antiviral and immunomodulatory activities. The addition of ribavirin to an alpha interferon, for example, may increase the long-term response rate in patients with hepatitis C. Other inhibitors of inosine monophosphate dehydrogenase may also be useful as adjuncts to alpha interferon in certain clinical settings, as may other classes of adjunctive therapy such as: interleukin-2, interleukin-2 analogs or derivatives, histamine, histamine analogs or derivatives; a monoclonal antibody or antibodies; a polyclonal antibody or antibodies; or any combination thereof.

Limitations of Interferon Treatment

These current antiviral therapeutics are, however, not without limitations. For example, the long-term success rate in the treatment of hepatitis C is estimated to be for: alpha interferon alone (≈10-15%); consensus interferon alone (≈10-15%); pegylated alpha interferon alone (≈20-25%); alpha interferon combined with ribavirin (≈30-40%); and alpha interferon plus a histamine-related compound (~30-40%). There is evidence that treatment with the combination of alpha interferon and ribavirin or histamine analogs may induce responses in patients who appeared not to be fully responsive to alpha interferon alone. Consensus interferon in high doses has been reported to induce responses in patients who failed to achieve sustained results on lower doses of alpha interferon.

Resistance and Side Effects

In a large percentage of patients, however, there is no significant antiviral activity by either alpha or consensus interferon, whether or not combined with another agent. The patients are said to exhibit primary viral resistance. In addition, a significant fraction of patients whose disease does respond initially do not have a sustained response after drug therapy has ceased. The patients are said to exhibit secondary viral resistance. Among those patients who fail to respond to alpha interferon, the majority also fail to respond to subsequent treatment with consensus interferon. The reasons for primary or secondary resistance are not completely understood but may involve significant variations in blood levels of the interferon, the development of antibodies directed against the interferon, the genetic features of the virus and/or the patient, or changes in the virus and/or the patient.

Furthermore, not all patients can tolerate therapy with an interferon, whether alone or in combination with an adjunctive therapeutic agent, because of adverse side effects. Some side effects may be worsened by the addition of ribavirin, interleukin-2, or other adjunctive therapies now in use or under development. Moreover, certain patients who have been characterized initially as "resistant" to alpha interferon appear to respond to alpha interferon when a second or subsequent course of therapy is given, suggesting that the patient may have been inadequately treated during the earlier course of therapy or otherwise not truly resistant. Patients failing alpha interferon who are subsequently "responsive" to consensus interferon may be in a similar category, i.e., inadequately treated during the initial course of therapy. Inadequate treatment can easily occur if the initial duration of treatment is too brief or the dose for a particular patient is too low, leading to misleading or false conclusions regarding viral resistance.

Problems with Short-Term Administration

In addition, whether used as monotherapies or as part of combination therapies, currently available injectable interferons are inconvenient for patients to administer over a long period of time. The principal reason is the required frequency of injections, from one or more times per day to once per week. The dose of a drug in a formulation intended for short-term usage and frequent administration can be rapidly changed. Nonetheless, there is still a significant risk of peaks in drug concentration in blood or tissues (occurring immediately after or early in the dosing cycle) and troughs (occurring just before the next dose is to be administered).

This phenomenon can be particularly troublesome with an interferon formulated for short-term usage with frequent administrations required. With peak levels, there may be an increase the risk of troublesome side effects and with prolonged trough levels, there may be periods of time when there is little or no interferon activity is present in the blood or tissues.

In summary, any formulation of an interferon intended for short-term usage is usually highly adjustable with respect to the dose of the drug but also highly inconvenient for long-term administration.

Problems with Long-Term Administration

A sustained release preparation of an interferon with a depot form capable of delivering a biologically active drug at a stable rate for many months, or a year or even longer, would have many potential advantages. There are many potential forms of a sustained release preparation including but not limited to: an implantable, non-erodible device with a reservoir capable of holding the drug isolated from the tissues and then releasing the drug at a controlled rate systemically into the body, or locally into a single organ or site; an implantable erodible device or matrix with drug in or on the matrix capable of systemic or local delivery; a gel or other suspension containing the drug capable of controlled-rate systemic or local delivery; an external pump for IV delivery; a patch or other controlled-rate transdermal delivery system. The drug may be delivered as the unmodified molecule or coupled covalently or non-covalently to carriers, polymers, nonpolymers or other molecules, from which the original molecule is released in its original or still modified form. Those skilled in the arts will recognize that there are many other forms of chronic controlled-rate delivery systems that could be employed.

One of the potential advantages of any sustained release system would be the avoidance of frequent and painful injections, thereby minimizing the possibility that doses would be missed which could potentially lead to ineffective therapy. Another advantage would be the potential for maintaining stable or even fixed rate of delivery of a drug systemically or locally, thereby minimizing the chances for "peak-related" adverse effects and/or "trough-related" ineffective therapy.

There are also potentially significant disadvantages with any long-term depot. Any such formulation would necessarily involve, relative to a short-term daily or weekly dose, the administration of a relatively large and potentially very costly amount of drug. If there is occurrence in the patient of a severe side effect requiring an immediate reduction in the dose, such a reduction would be practically impossible or very difficult with any long-term sustained release preparation that had been implanted or injected. For a mechanical device, an erodible matrix, or a gel or other suspension it may be necessary to perform an invasive procedure to attempt to remove all or part of the administered drug. For all except the use of a mechanical device or transdermal patch, in fact, which hold the drug intact within a reservoir physically isolated from the body, it might be impossible to remove all of the drug. Accordingly, while long term administration of an interferon offers many advantages to a patient, any error in selecting the long-term dose level or long-term drug delivery rate could have very adverse and costly consequences.

Moreover, for patients with certain diseases such as viral hepatitis C, it may be desirable to individualize the dose as much as possible. Historically, patients have been treated with a fixed amount of interferon per week and such amounts have been maintained at the fixed level for many weeks or months in the absence of supervening side effects that mandated a reduction in dosage. Short-term delivery of an interferon offers the potential advantage of permitting doses to be adjusted readily, while long term administration of a fixed rate of drug delivered from, for example, a reservoir permits no adjustment at all.

In summary, a formulation of a drug, such as an interferon, used with a long term delivery system or device is highly convenient for ensuring stable delivery of drug, but is relatively or absolutely inflexible with regard to adjustment of the drug and potentially expensive or requiring invasive procedures to reduce the amount or eliminate the drug from the body altogether.

Advantages of the Present Invention

I have now invented an approach that addresses the problems in the prior art in the long-term use of a drug, e.g. an interferon, for the treatment of disease of warm-blooded animals that require long term administration to treat the disease or condition, e.g. one that is interferon-responsive.

My invention maximizes the probability of delivering an effective dose of a drug, such as an interferon, to a warm-blooded animal with, e.g. an interferon-responsive disease or condition and further maximizes the chances of delivering a safe dose of the drug, such that the dose is minimally toxic and therefore tolerated by the recipient.

My invention further facilitates the selection of a safe, tolerated and effective dosage of a drug, e.g. an interferon, to be delivered to a warm-blooded animal by a long-term delivery system and facilitates dose-individualization of the drug for an individual patient in the setting of long-term administration using a long-term delivery system.

My invention also minimizes or eliminates the need to alter the rate or change the dose-rate of the drug once long-term dosing has commenced with a long-term delivery system.

Further, in the event that dose- or rate-adjustment is required, my invention aids in minimizing the negative impact on therapy and cost of any such adjustment in dose or rate after the commencement of dosing with a long-term delivery system.

My invention also provides for combination therapy using, for example, interferon and one or more non-interferon adjunctive therapeutic agents or even a second, structurally distinct interferon.

SUMMARY OF THE INVENTION

One aspect of the invention is a method for the treatment of a disorder, e.g. an interferon-responsive disorder, in a warm-blooded animal. The method comprises administering at least one drug, e.g. an interferon, formulated for short-term use, adjusting the dosage of the short-term formulation to increase and preferably maximize therapeutic response while simultaneously decreasing and preferably minimizing adverse side effects, and subsequently selecting a dosage to be administered with a long-term delivery system and long-term formulation suitable for use in the long-term delivery system. Thereafter the long-term dosage is delivered with the long-term delivery system and, if necessary, the dosage is subsequently adjusted with the long-term formulation and long-term delivery system to further maximize therapeutic response while simultaneously minimizing adverse side effects.

Another aspect of the invention is a method for individualizing a dose of a drug, such as an interferon, in the treatment of a disorder, e.g. an interferon-responsive disorder, in a warm-blooded animal. The method allows a physician to establish a dosage for treating a specific patient for his or her individual needs over the length of treatment. The method comprises administering at least one drug, e.g. an interferon, formulated for short-term use, adjusting the dosage with the short-term formulation to increase and preferably maximize therapeutic response while simultaneously decreasing and preferably minimizing adverse side effects in a plurality of patients and determining the most commonly identified optimal dosage in a sufficiently large population of such patients to define this dosage as a unit dose. Subsequently, using a long-term formulation and a long-term delivery system, at least one unit-dose, optionally with one or more fractional unit doses, is administered such that, in aggregate, the optimal dosage identified during dosing with the short-term formulation can be approximated with the unit-dose/fractional unit-dose combination using the long-term formulation and long-term delivery system. Thereafter, a dosage is selected and administered with a long-term formulation in the long-term delivery system. The long-term dosage is administered via the long-term delivery system and the dosage of the long-term formulation via long-term delivery system is optionally adjusted to further maximize therapeutic response while simultaneously minimizing adverse side effects.

Another aspect of the invention is a method of manufacturing a long-term delivery system for delivering a drug over time. The method comprises preparing a long-term delivery device designed for delivery of a drug at a specified constant rate over time, the rate being determined to be a standard dosage rate to treat a disease state in the patient treatable over time by the drug, and preparing a second long-term delivery device designed for delivery of the same drug at a specified constant rate over time, which rate is a fraction of the standard dosage rate of the first device. Each device is suitable for presentation to a patient in need thereof alone or in combination, depending on the dosage rate or fractional dosage rate determined to be appropriate for the patient. The patient may then have a device delivering a standard dosage rate or some fraction lesser or greater than the standard dosage rate, depending on the characteristics of the patient, e.g. age, gender, weight, physical condition, etc.

Still another aspect of this invention is a kit useful for delivery of a constant amount of a drug thereof over time, wherein the amount of drug delivered to an individual patient within a population can be adjusted to the patient's individual needs for treatment. The kit comprises (a) at least one long-term delivery device designed for delivery of a drug at a constant rate over time, the rate being determined to be a unit rate as a standard dosage to treat a disease state in a patient in the population over time, and (b) at least one long-term delivery device designed for delivery of the same drug at a relatively constant rate over time, which rate is a fraction of the standard dosage rate, wherein each device in the kit is suitable for presentation to a patient in need thereof alone or in combination with an identical device or the device having a different delivery rate depending on the dosage rate determined to be appropriate for the patient. Alternatively, the kit comprises at least two long-term delivery devices designed for delivery of the same drug at the same or different constant rates over time, for which each rate is a fraction of the standard dosage rate, wherein each device in the kit is suitable for presentation to a patient in need thereof along or in combination with an identical device or the other device, depending on the dosage rate determined to be appropriate for the patient.

The invention is particularly valuable for the administration of omega interferon, but also encompasses the use of other drugs, e.g. interferons (or mixture thereof) that bind to and activate interferon receptors in warm-blooded animals with an interferon-responsive disease or condition. The invention also encompasses combination therapies of drugs, such as an interferon, or mixture thereof, and one or more non-interferons or even a second, structurally distinct interferon. The invention is particularly valuable for the administration of omega interferon to treat hepatitis C.

The invention is also useful for the administration of any highly potent molecule, e.g., cytokines, hormones, or congener or analog thereof, for which there are significant side effects that can be lessened and/or benefits that can be increased by the appropriate selection of short and long-term doses. The invention is particularly valuable for the administration of: growth hormone to treat growth defects and injuries to tissues; sex hormones such as luteinizing hormone or related releasing factors such as luteinizing hormone releasing hormone to treat endocrine disorders or cancer.

The invention is not limited by the number of different formulations. If a relatively smaller amount of, for example, interferon (whose duration in the body is measured in hours to days) is delivered by a formulation that can be used to assess the safety, tolerability, and efficacy of a larger amount of the same or different interferon delivered in the same formulation (but whose duration in the body is measured in weeks or months because of the larger amount provided), the current invention also encompasses this differential use of a single formulation to effect both short-term and long-term therapy. The larger amount will differ from the smaller amount by a preferred factor of at least four, more preferred at least twelve, and most preferred twenty-four or higher.

The therapeutic method of the present invention is amenable to intermittent or repeated use for the treatment of acute, chronic, remitting or relapsing diseases or conditions.

The therapeutic method of the present invention can be utilized if there is little or no delay in transitioning from short- to long-term therapy (minutes to days) or if there is a delay in transitioning from short- to long-term therapy (weeks to months). For example, short-term dosing with an interferon such as omega interferon could occur at a single dose level during days 1-14 of therapy and, based on the information obtained regarding signs, symptoms, and laboratory values during these first 14 days, appropriate long-term therapy could begin on day 15. Alternatively, and again by way of example, short-term dosing could occur during days 1-14, followed by a second but different short-term dosing from days 15-28, and long-term therapy could begin on day 29. In another example, information regarding responsiveness and tolerability to a short-term formulation of an alpha or gamma interferon could be obtained during 1-12 months of prior treatment. During this 1-12 month period, the dose of alpha or gamma could remain the same or be altered according to patient response and adverse side effects. Thereafter, a period of indeterminate length without treatment could occur. Treatment could be halted for any of several reasons including incomplete therapeutic response or unacceptable adverse events. For example, then, a no-treatment period could also be of 1-12 months duration. Thereafter, but still based on the information obtained during the 1-12 months of prior active treatment, therapy with a long-term dosing formulation of the same or a different interferon could begin.

Other aspects of the invention may be apparent to one of skill in the art upon further reading the following specification.

DETAILED DESCRIPTION OF THE INVENTION

Method of Treatment

Figure 1:
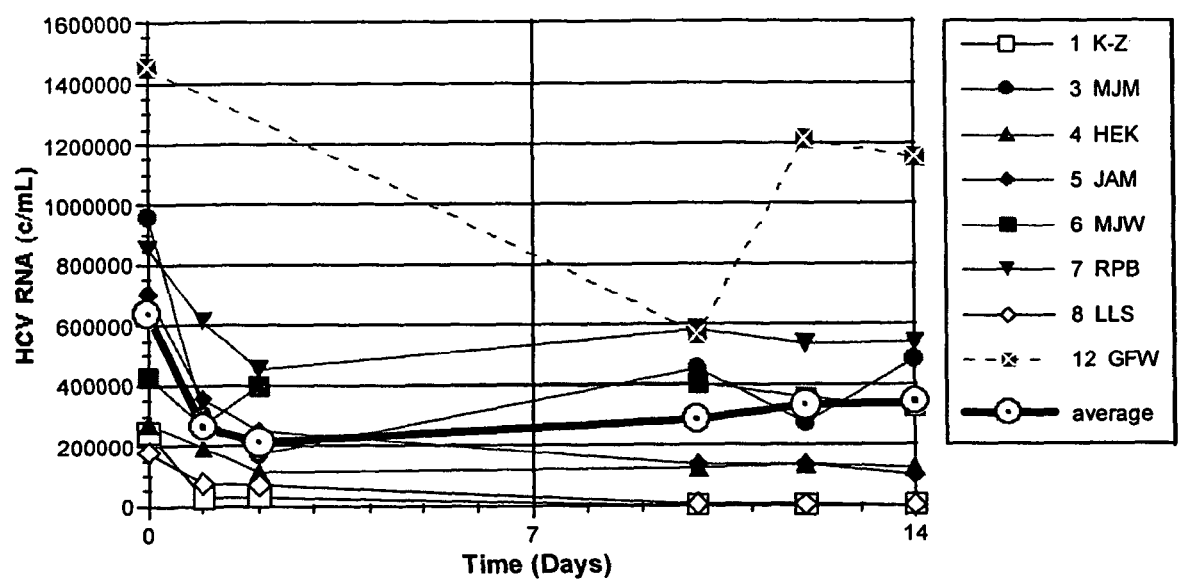
FIG. 1 is a graph showing the change in HCV RNA levels versus time in individual human subjects with chronic hepatitis C infection resistant to 3-12 months of treatment with alpha interferon with or without ribavirin.

One aspect of the invention is a method for the treatment of a disorder, e.g. an interferon-responsive disorder, in a warm-blooded animal. The method comprises the following steps:
administering at least one drug, e.g. an interferon, formulated for short-term use, adjusting the dosage of the short-term formulation to improve the therapeutic index in a patient with a disease or condition responsive to the drug, thereby achieving a desirable therapeutic response with no, few or clinically acceptable adverse side effects;
based on the clinical information gained during administration of the short-term formulation, selecting the dosage to be administered initially as a long-term formulation and selecting the time at which the transition from short-term formulation to long-term formulation occurs, and thereby retaining or further enhancing therapeutic index
based on the clinical information gained during administration of the short-term formulation, selecting the time at which the transition from short-term formulation to long-term formulation occurs, and thereby retaining or further enhancing therapeutic index
thereafter adjusting the dosage of the long-term formulation, preferably but not necessarily upwards, if and as required.

The method of the current invention has several benefits. Consider, for example, the clinical setting in which a long-term delivery system is used with a drug that has the potential for serious toxicity, has the potential for different or progressive toxicities over time, has a narrow or even no therapeutic window (i.e., the effective dose-range is similar to or overlaps the toxic dose-range), is very expensive, or a combination of these factors. Currently, interferons are costly, have a narrow or no therapeutic window and can cause different toxicities over time. Therefore, an interferon represents one such drug. For such drugs, the selection of dose or changes thereof should be made with great care.

The treatment of hepatitis with an interferon is an example of one clinical setting in which an interferon-responsive disorder must be treated typically for several months to a year or longer. If a health-care provider begins treatment with a long-term delivery system, e.g., where weeks or months of treatment are possible with a single administration, then the selection of the long-term dose is of critical importance.

It is worth noting that the administration of an interferon for long-term delivery will generally involve the delivery of drug at more or less a fixed rate throughout the course of therapy if system start-up or shut-down effects, if any, are ignored. Long-term delivery systems such as gels or polymers, once injected or implanted, typically erode or dissolve at rates that cannot be changed without surgical intervention. Implantable pumps that cannot be externally programmed or adjusted to change the rate of delivery would require replacement or removal to effect a dose change.

Consider the example where a long-term dose is selected and is effective but causes severe or serious side effects shortly after the initiation of treatment, e.g., after only a small percentage of the total dose is delivered. Then, in order to protect the patient it may be necessary to remove part or all of the drug-delivery system in order to reduce the dose or dose-rate. Alternatively, consider the example where a long-term dose is selected and is effective and initially well tolerated but a serious or severe adverse effect appears later, but at a time when a clinically and economically meaningful percentage of drug still remains in the system. Then, in order to protect the patient it may still be necessary to remove part or all of the drug-delivery system in order to reduce the dose or dose-rate.

Such removal may or will:
involve procedural risk, expense, and time for the patient
waste some or all of the (expensive) drug that had been administered
reduce the chances for effective therapy
may induce the patient or health-are provider to abandon a potentially convenient, safe and effective therapy.

Therefore, it is very desirable to avoid the early or otherwise risky or wasteful removal of the long-term delivery system. The method of the current invention makes possible the achievement of this goal.

The benefits of the method of the current invention may be further exemplified. In the treatment of a disease or medical condition it is generally desirable to effect a therapeutic response as rapidly as is safely possible. This means that the onset of drug action is appropriately rapid. However, when a sufficiently severe adverse side effect occurs, the typical response is to stop administration of the offending drug and to wait for the offset of drug action. Clearly, it is desirable to have a rapid offset if a severe side effect occurs. Preferably the offset will be measured in minutes to a few hours. Examples of drugs with relatively rapid onset, possible severe side effect, but relatively rapid offset include the following drugs administered by injection or infusion in a suitable short-term formulation include heparin that induces bleeding or penicillin that induces an allergic response.

Four examples of drugs administered by injection or infusion that have less rapid offset (many hours to days or weeks) but are associated with serious side effects include cyclophosphamide and bone marrow cellular depletion, cyclosporine and acute infection, interferons and granulocytopenia, or interferons and depression or suicidal ideation. Any of these side effects may be sufficiently severe to put a patient's life in jeopardy or to result in the death of a patient. In the presence of such adverse side effects it may be necessary in these four clinical settings, respectively, to stop the offending drug and to administer granulocyte colony stimulating factor to increase cell count, to administer antibiotics to combat infection, wait until granulocyte count returns to normal before resuming treatment at a lower dose, or to hospitalize the patient and give antidepressants, electric shock treatment or even maintain constant physical restraint.

In the case of an interferon dose that could deliver drug for weeks or months, the appearance of granulocytopenia can be rapid, occurring within a matter of a few days to weeks. Halting therapy or immediately reducing the dosage is necessary in order to reduce the risk of serious infection. An injectable form of interferon typically persists in the body for several hours or, in the case of pegylated interferons, for a week or more. In either case, the use of a short-term injectable can be modified or halted immediately after granulocytopenia is detected. Recovery is typically rapid, within days, and therapy can be resumed or continued at a lower dose. However, if a multimonth form of the interferon were present instead in the form of, for example, an injected gel or polymer or implanted pump, then granulocytopenia would persist or worsen during continued presence of the drug—until and unless the gel, polymer, or pump is surgically excised or extracted. For the reasons stated above, a sudden and unplanned removal of a long-term delivery system is very undesirable.

With the method of the present invention, the short-term formulation is administered and adjusted until the desired therapeutic effect is achieved and, if adverse side effects occur acutely during a few days or weeks after beginning therapy, the dosage is lowered to reduce these effects. Then, and only then, the long-term dose is selected and the long-term delivery system injected or implanted, thereby retaining the benefits of the prior short-term dose selection.

In the case of an interferon dose that could deliver drug for weeks or months, the appearance of, for example, suicidal ideation after several weeks or months of interferon therapy would constitute a medical emergency. The method of the current invention can reduce this risk. By applying the method described herein, treatment with the short-term dosing form could be continued for many weeks or months in selected patients and after the risk of depression or suicidal ideation was judged to have passed or to be low, then an appropriately selected long-term dose can be administered.

Those skilled in the art will recognize other benefits of the current invention not described in the examples contained herein.

While the various aspects of this invention relate to the long-term delivery of drugs generally, the details of the invention are explained using interferons, particularly omega interferon, as the drugs of choice. The term "interferon" (or "interferons") is meant to be interpreted in its broadest sense, i.e. glycoproteins that are potent cytokines, i.e. hormone-like low molecular weight proteins that regulate the intensity and duration of immune responses and are involved in cell-to-cell communications. The interferons possess complex anti-infective (e.g. antiviral), immunomodulating, and antiproliferative activity. Thus, the interferons are used for treating disorders of viral origins, disorders of the immune systems, and disorders generally referred to as cancers, i.e. malignant neoplasms. These disorders are referred to as "interferon-responsive disorders." The types of interferon ("IFN") include both naturally-occurring and recombinant IFN, e.g. alpha(alfa)-IFN, beta-IFN, gamma-IFN, tau-IFN, consensus IFN, leukocyte-IFN, omega-IFN, and the like. The term also includes a modified IFN such as one that is modified to include one or more polyethylene glycol ("PEG") molecules or a PEG-fatty acid moiety attached by covalent or non-covalent binding. Omega-IFN is preferred.

Typical suitable alpha interferons include recombinant interferon alpha-2b such as Intron-A interferon available from Schering Corporation, Kenilworth, N.J., recombinant interferon alpha-2a such as Roferon interferon available from Hoffmann-La Roche, Nutley, N.J., recombinant interferon alpha-2C such as Berofor alpha 2 interferon available from Boehringer Ingelheim Pharmaceutical, Inc., Ridgefield, Conn., interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain, or a consensus alpha interferon such as those described in U.S. Pat. Nos. 4,897,471 and 4,695,623 and the specific product available from Amgen, Inc., Newbury Park, Calif., or interferon alpha-n3, a mixture of natural alpha interferons made by Interferon Sciences and available from the Purdue Frederick Co., Norwalk, Conn., under the Alferon Tradename or alpha interferon analogs such as described in U.S. Pat. Nos. 6,204,022 and 5,939,286.

The term "interferon beta" or "beta-interferon" or "β-IFN" means the proteins described in U.S. Pat. Nos. 4,820,638 and 5,795,779.

The term "interferon gamma" or "gamma interferon" or γ-IFN" means the proteins described in U.S. Pat. Nos. 4,727,138; 4,762,791; 4,845,196; 4,929,554; 5,005,689; 5,574,137; 5,602,010; and 5,690,925.

The term "interferon tau" or "tau interferon" or "ρ-IFN" means the proteins described in U.S. Pat. Nos. 5,939,286; and 6,204,022.

The term "interferon omega" or "omega interferon" or ω-IFN as used herein means the species-specific protein that is described in U.S. Pat. Nos. 5,120,832 and 5,231,176. It can inhibit viral replication, cellular proliferation, and modulate immune response, even in settings or patients where alpha interferon is not effective or has limited effectiveness. Omega-IFN is a naturally occurring interferon which has limited homology to the alpha interferons (65%) and even less homology to the beta interferons (35%), i.e., omega interferon is structurally distinctive. Omega interferon appears to bind to what has been termed the "α-β interferon receptor" as judged by in vitro testing. Using genetic engineering techniques, recombinant omega interferon is manufactured in a form that is suitable for use in animals, including humans. It has been shown that antibodies developing in animals exposed to alpha interferon do not cross react with omega interferon, i.e., that omega interferon is immunologically distinctive. Moreover, it has been demonstrated in vitro in cells infected with the immunodeficiency virus that the patterns of gene signaling induced by alpha and omega interferon are different, i.e., that omega interferon is also functionally distinctive.

The method may be used in any warm-blooded animal that has an interferon-responsive disorder. The animals may be livestock, household pets, or preferably humans. Thus, the method has both veterinary and human medicinal uses. Livestock treatable by this method include horses, cattle, swine, sheep, goats, and the like. Household pets include cats, dogs, rabbits, and the like. Preferably, however, the method of the invention has its primary application in the treatment of humans, both male and female, young and old.

The diseases treatable by the method of this invention include those of infectious (e.g. viral), immunologic, or proliferative origins that in some portion of the population may be treatable by the administration of an interferon. Diseases of viral origins are those caused by a virus such as those set forth in Stedman's Medical Dictionary, 26th Edition, particularly hepatitis B, C, or D, especially hepatitis C. Immunologic diseases are those of where the immune system of a patient is unbalanced. These diseases include, for example, chronic granulomatous disease, acquired immunodeficiency syndrome, multiple sclerosis, systemic lupus erythematosus, and scleroderma. Proliferative diseases are generally those that include various types of malignant neoplasms, most of which invade surrounding tissues and may metastasize to several sites. These are often referred to as cancers and include, e.g., condyloma accuminata, hairy cell leukemia, malignant melanoma, multiple myeloma, follicular lymphoma, non-Hodgkin's lymphoma, cutaneous T-Cell lymphoma, chronic myelogenous leukemia, basal cell carcinoma, carcinoid syndrome, superficial bladder cancer, renal cell cancer, colorectal cancer, laryngeal papillomatosis, actinic keratosis, or AID's related Kaposi's sarcoma. Other proliferative diseases include fibrosis of tissues or organs such as the lung or liver. Tuberculosis is also treatable by the method of this invention.

In carrying out the method of treatment of this invention, a drug formulated for short-term use is administered to a patient in need thereof and is adjusted to improve the therapeutic index. This adjustment may be done in one or a plurality of patients using measurements well known in the art to show the drug is working therapeutically and whether there are known or suspected side effects. The term "short-term use" means that the drug is used as a formulation designed to be delivered to a patient multiple times to obtain the desired effect. For example, the drug may be delivered by injections, infusion, implant, transdermally, orally, parenterally, or by inhalation. For example, an interferon may be delivered intravenously, intramuscularly, or subcutaneously once every 6 hours, 12 hours, or 24 hours. Such dosing will generally show a concentration profile similar to that shown in FIG. 3. By changing the dosage frequency the amount in the blood may change as shown in FIG. 4. The dosage used over the short term is then adjusted to maximize the therapeutic effect and minimize the adverse side effects. The dosage has two components: the dose level and the dose rate. The dose level is the total amount of drug delivered to a patient, while the dose rate is the amount delivered to the patient per time unit.

For example, if omega interferon is administered by a standard route (e.g. IV, IM, subcutaneous), the following important parameters are useful to maximize the therapeutic response while minimizing the adverse side effects and select a safe, tolerable, and effective dose for long-term administration of omega interferon in patients with chronic hepatitis C ("HCV"): number of target cells, rate constant for death of target cells, rate of production of target cells, fractional reduction in de novo rate of infection of target cells, rate constant for de novo infection of target cells, viral load (i.e. HCV RNA levels), number of productively infected cells, rate constant for death of infected cells, fractional reduction in production of virions by infected cells, rate of production of virions by infected cell, rate constant for clearance of hepatitis C virions. These are described in more detail hereinafter.

Referring to FIG. 1, one sees a graph showing the change in HCV RNA levels versus time in individual subjects with chronic HCV infection resistant to 3-12 months of treatment with alpha-IFN, with or without Ribavirin. Each patient was treated short-term for various periods of time with 15 µg/dose of omega-IFN, with 3 doses per week on days 1, 3, and 5 of each 7 day week (both ordinate and abscissa linear scale) Three of 8 patients manifested undetectable HCV RNA after treatment with omega interferon. In resistant patients it appears that the maximal decrease in viral load may be apparent within the first few days of treatment, potentially as early as two days after the commencement of treatment. The tolerability and safety profile is reasonably well established within 4 weeks after beginning treatment.

Figure 2:
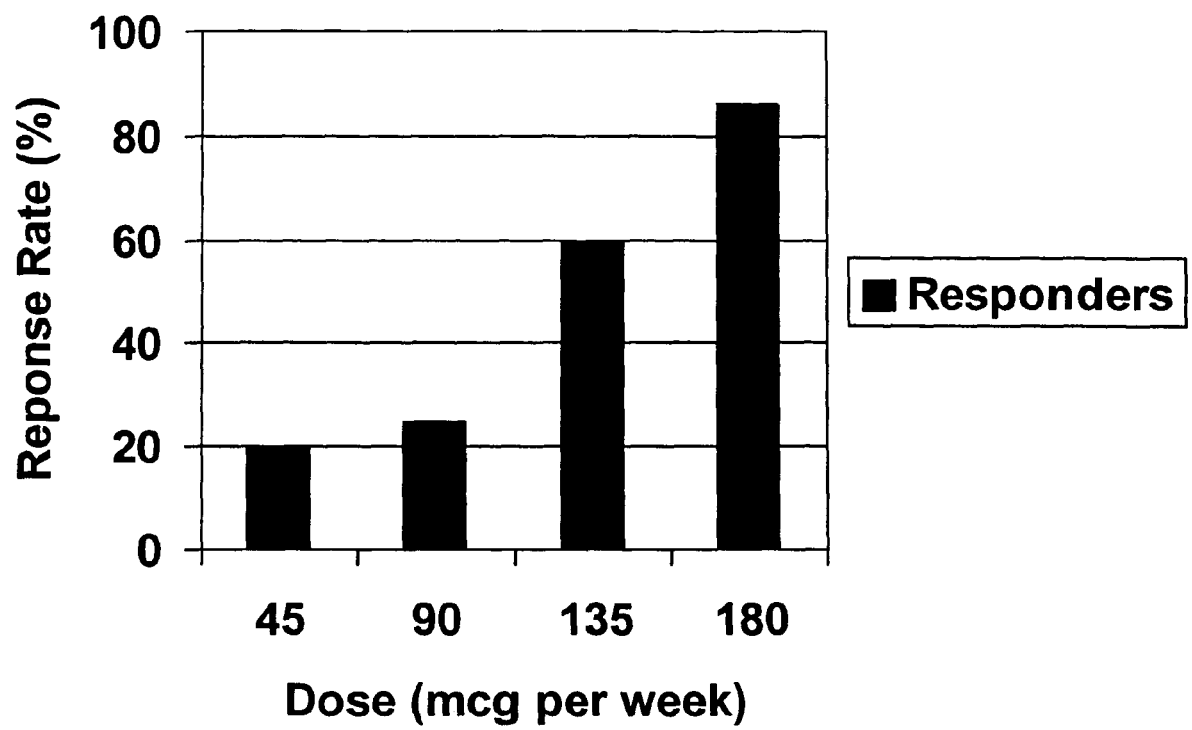
FIG. 2 is a graph showing that increasing doses of omega interferon produce progressively larger viral clearance rates (response rate) in patients with chronic hepatitis C infection who were previously untreated with an interferon.

In FIG. 2, a graph is presented that shows an increase in the response rate as measured by complete viral clearance in human patients with chronic HCV infection previously untreated with an interferon. Each patient was treated short-term for various periods of time with the dosages shown in FIG. 2 of omega-IFN per week. 3 doses were given per week on days 1, 3, and 5 of each 7 day week thereafter. The tolerability and safety profile is reasonably well established within 4 weeks after beginning treatment.

Figure 3:
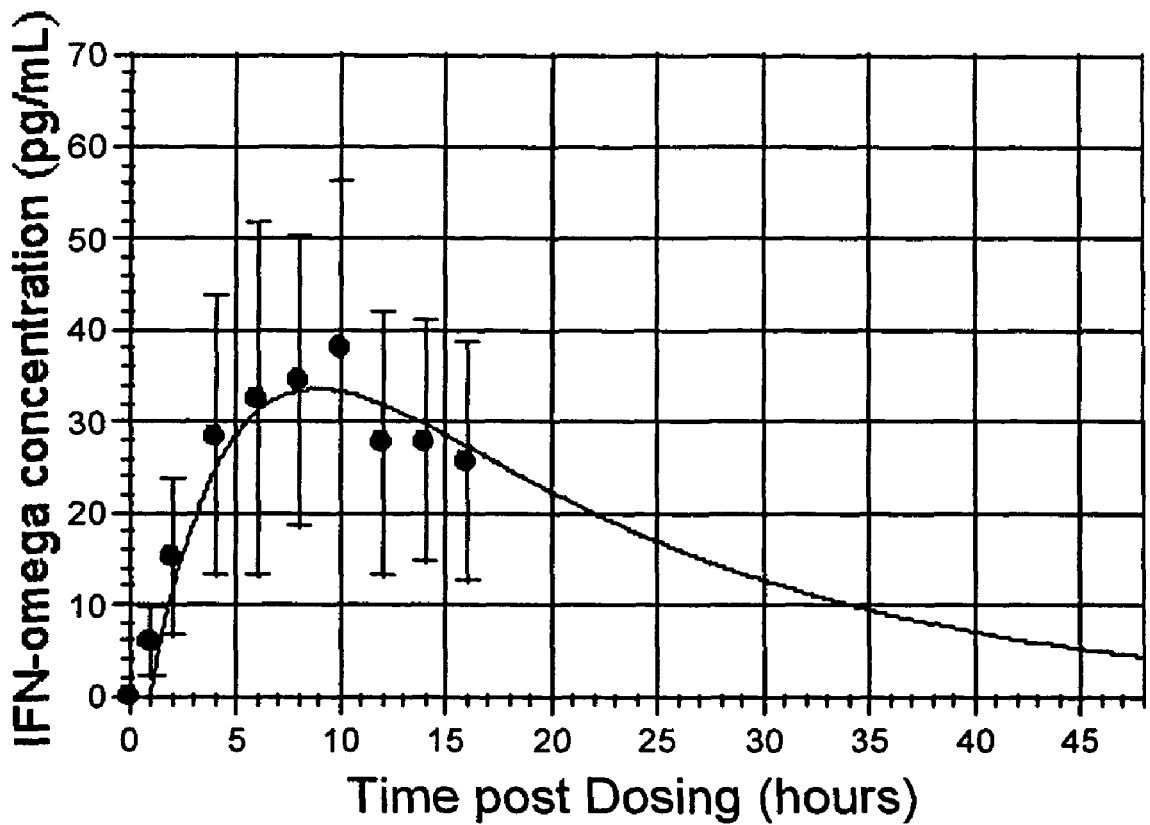
FIG. 3 is a graph showing the pharmacokinetics of omega interferon (plasma concentration vs. time) after a single dose of omega interferon in humans. The median half-life of absorption is 3.1 hours; the median half-life of elimination is 11.4 hours.
Figure 4:
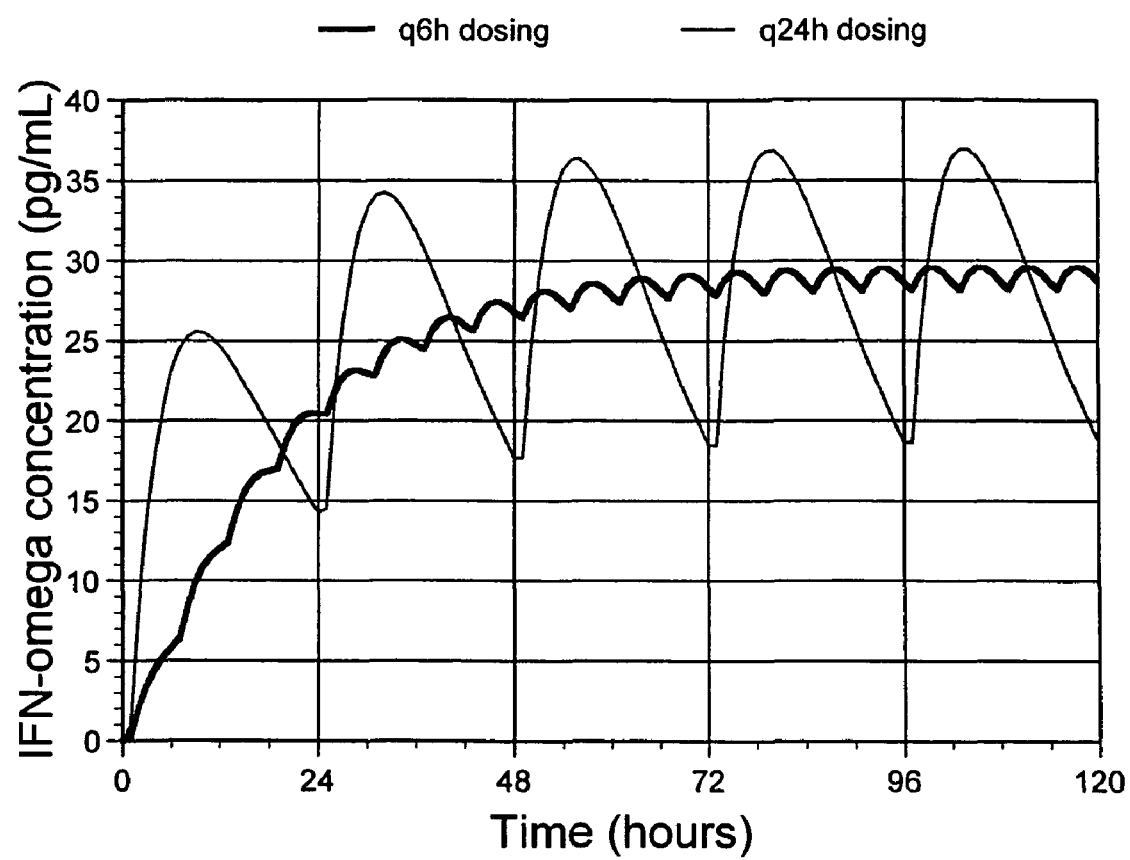
FIG. 4 is a graph showing the calculated pharmacokinetic profile of omega interferon with once daily (q 24 hour) and 4 times daily (q 6 hour) dosing cycles, with the same total daily dose of 15 μg.

FIG. 3 presents a graph showing the pharmacokinetics of omega-IFN after a short-term dose of omega-IFN in humans. The median half-life of absorption is 3.1 hours, while the median half-life of elimination is 11.4 hours.

Turning now to FIG. 4, one sees a graph showing a calculated pharmacokinetic profile of omega-IFN with once daily (q 24 hour) and 4 times daily (q 6 hour) dosing cycles, with the same daily dose of 15 µg. With 4 times daily dosing the variation in omega plasma levels from trough (approximately 28.1 pg/mL) to peak (approximately 29.9 pg/mL) is approximately 6% of the peak value. From the mid-range value of approximately 29 pg/mL, the variation to peak or to trough is approximately 3%. Such a small variation is effectively a steady-state and is achieved within 72 hours after the commencement of dosing with omega interferon. The variability can be reduced to even smaller values by reducing the dose and increasing the frequency of administration. This steady-state pattern effectively replicates that which would be observed with a long-term delivery system emitting an interferon at a fixed rate, where the rate was adjusted to achieve the plasma level as shown.

With the information shown in FIGS. 1-4 and other information, one can adjust the dosage of the short-term formulation to increase and preferably maximize the therapeutic effect and decrease and preferably minimize the adverse side effects and select a dosage to be delivered over the long-term, i.e. from a month to a year or more, using a long-term delivery formulation that delivers the drug at a controlled rate over time. While it may be desirable to commence long-term therapy immediately upon cessation of short-term therapy, such immediate transition is not always required and there may be a delay of days to months in commencing long-term therapy. In this method, the interferon delivered in the short term is generally the same as the interferon that will be delivered to the patients over the long-term, although an interferon that differs from that given for the short-term may be administered over the long term. Once a formulation for short-term administration is established, the same, or essentially the same formulation, may be used for long-term administration, albeit packaged for long-term controlled releases. Alternatively, the long-term formulation may be different to account for the needed changes for the longer, controlled-release characteristics. In some cases, if the attending physician believes it appropriate, more than one interferon or even different interferons (e.g., alpha interferon and pegylated alpha interferon) may be used for the short-term or long-term administration, with each interferon being formulated the same or each formulated differently. If useful, the dosage can be adjusted upward by administering a long-term formulation that provides a fraction of the dosage rate released by the first long-term formulation. Long-term formulations that are useful for delivering the desired dosage over time include any formulations or devices that aid in the delivery of the drug in a controlled manner to the patient at the rate desired. These formulations may be internal (i.e. implantable in the patient to deliver the drug internally) or external (i.e. delivers the drug internally with the formulation located external such as a pump or chronic intravascular infusion system or transdermal system) to the patient. While oral or inhalation devices may be used, they don't lend themselves to easy long-term use. If internal (implantable or injectable) the formulation may be bioerodible, e.g., a gel or pellet, or nonbioerodible, e.g., a mechanical device such as a pump.

An example of a suitable nonbioerodible formulation or device is one employing the DUROS® system (ALZA Corporation), which is a miniature drug-dispensing pump currently made principally from titanium and which can be as small as a wooden matchstick.

The DUROS® pump operates like a miniature syringe loaded with a drug inside the drug reservoir. Through osmosis, water from the body is slowly drawn through a semipermeable membrane into the pump by a salt or other suitable osmotically active substance residing in the engine compartment. This water is absorbed by the osmotic substance which then swells and which slowly and continuously pushes a piston, dispensing the correct amount of drug out the drug reservoir and into the body. The osmotic engine does not require batteries, switches or other electromechanical parts in order to operate. The amount of drug delivered by the system is regulated by many factors, including, for example, the materials used in manufacturing, the membrane's control over the amount of water entering the pump, the strength of the osmotic agent, the frictional resistance to motion of the piston, the size and shape of the reservoir, the size, shape, and length of the orifice(s) through which the drug(s) exit the pump, the formulation and type of the drug(s) and whether the formulation is a liquid, suspension, or gel, and pressures generated within the device to expel drug(s) or counter-pressures generated in the tissues that resist such expulsion.

Other useful long-term delivery formulations may be prepared using the ALZET® technology developed by the ALZA Corporation. These formulations may be delivered externally. The details of the ALZET technology may be found at www.alzet.com.

Patents that provide useful guidance in preparing long-term delivery devices that may be useful in the methods and kits of this invention include those which are assigned to Alkermes. Other patents include those assigned to ALZA Corporation (now a subsidiary of Johnson and Johnson, Inc.), particularly relating to their "DUROS®" technology. Representative patents useful for the various aspects of this invention include the following U.S. Pat. Nos. 5,529,914; 5,858,746; 6,113,938; 6,129,761; 5,985,305; 5,728,396; 5,660,847; 5,112,614; 5,543,156; 5,443,459; 5,413,572; 5,368,863; 5,324,280; 5,318,558; 5,221,278; 4,976,966; 4,917,895; and 4,915,954. All are incorporated herein by reference.

Figure 5:
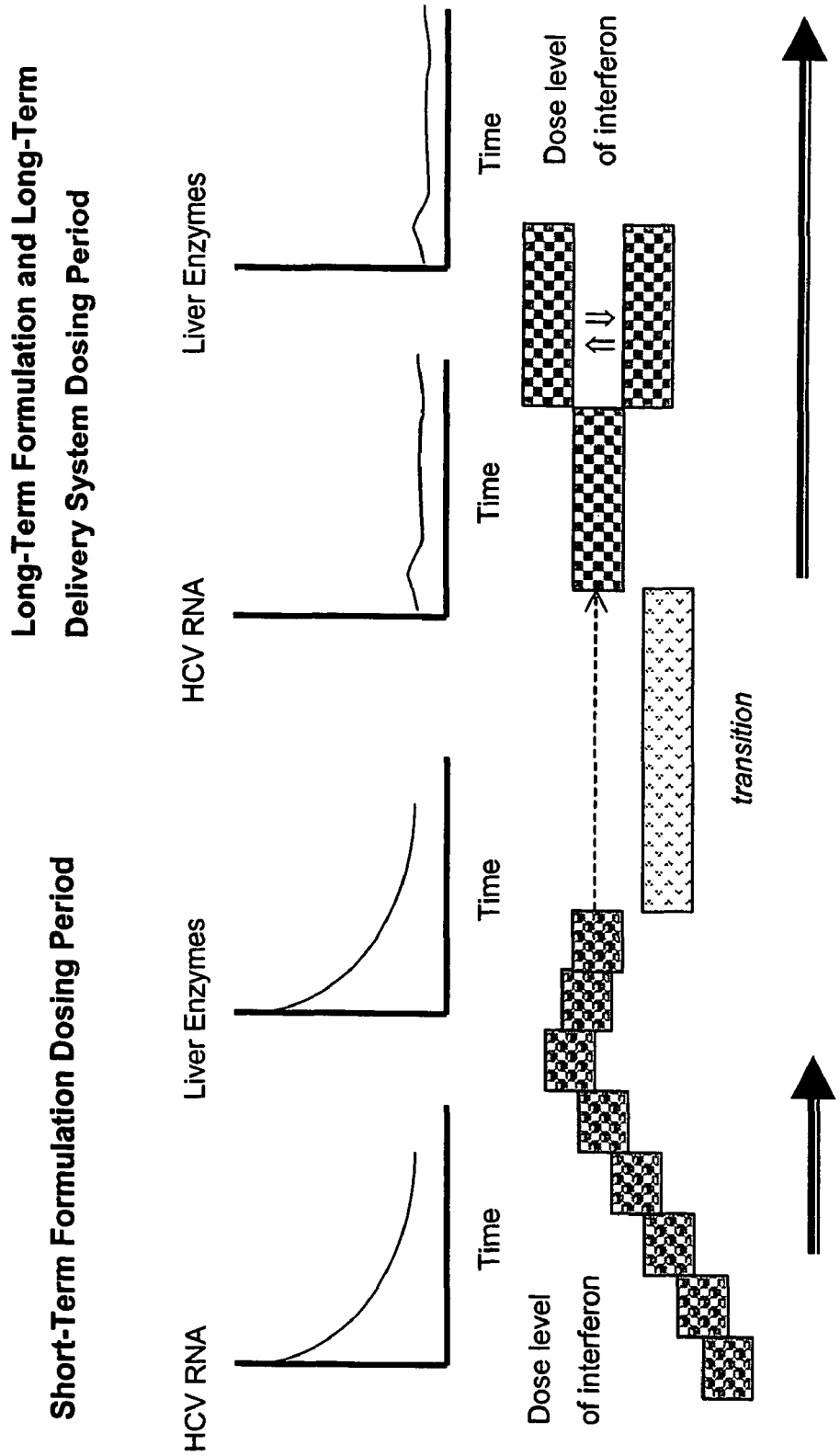
FIG. 5 is a depiction of one sequence of events in adjusting the dose using the short-term formulation 1, selecting the dose level for use with long-term formulation 2 and its associated long term delivery system. The period of transition can be of any duration.

The method of treatment, e.g. of HCV, can be further visualized with reference to FIG. 5. The figure is divided into a short-term formulation dosing period and a long-term formulation dosing period. During the short-term formulation dosing period the dose level of omega interferon is adjusted to assess both initial antiviral response (shown hypothetically in the graphs of HCV RNA and liver enzymes over time) along with safety and tolerability. The IFN dose is adjusted to achieve maximal antiviral effects with acceptable safety and tolerability. This process is represented by the series of stepped boxes showing a maximum dose with a slight reduction. With the dose identified the patient is then maintained on the dose during a transition, after which the long-term formulation dosing takes places. The short-term formulation is delivered first, and the long-term formulation is subsequently delivered either with or without an overlap of dosing with the short-term and long-term formulations. If there is no overlap, the delivery of the long-term formulation may be deferred for very brief periods of time (seconds to days) or longer periods of time (a week to several months). The long-term delivery is done with a long-term formulation and one or more fractional modules (or several fractional modules). The patient is monitored for the suppression of viral replication (as shown by the hypothetical graphs of HCV RNA and liver enzymes over time) as well as the prevention of long-term adverse sequelae of HCV infection including cirrhosis and liver cancer. The long-term treatment may be adjusted up with another equipotent formulation or a fractional module dosage form or may be adjusted down by providing one or more fractional module dosage forms after the device ends administration. Preferably a controlled-release dosage per time unit selected for long-term formulation is about equivalent to the dosage release over a time unit for the short-term formulation. For example, if the short-term administration is 30 mg in 24 hours, then the long-term formulation would be designed to release about 1.25 (30÷24=1¼) µg/hour. On the other hand, the long-term dosage per unit of time may be more or less than the short-term administration.

Individualizing Doses

Another aspect of the invention is a method for individualizing doses of a drug delivered over an extended period of time to a patient in need of such treatment. This is particularly valuable for patients receiving implantable devices. The method is particularly useful for interferon, especially omega interferon. For example, the method comprises determining the most commonly identified optimal dosage (i.e. the dose-level or dose-rate) in a sufficiently large population of recipients to define a unit dosage; and subsequently, using a long-term formulation for controlled release, administering at least one unit-dosage optionally with one or more fractional unit dosages, such that, in aggregate, the optimal dosage identified during dosing with the short-term formulation can be approximated with the unit-dosage/fractional unit-dosage combination using the long-term formulation. The desired dosage is selected for long term delivery and thereafter administered with the long-term delivery formulation, which can be optionally subsequently adjusted, if necessary, to further maximize therapeutic response with simultaneously minimizing adverse side effects. This is discussed further under "Dosimetry Protocol." The principles expressed in the Method of Treatment section apply the method for individualizing doses.

Convenient fractional unit-dose devices can be selected from 0.1, 0.2, 0.3, 0.4, 0.5, 0.6, 0.7, 0.8, 0.9. Smaller or larger values less than 1.0 can also be selected. With one unit-dose formulation and one fractional unit-dose module, e.g., 0.4, it is possible, by using one or two of these items, to attain doses of 0.4, 0.8, 1.0, 1.4 and 2.0 unit-doses. With one unit-dose formulation and two fractional unit-dose modules, e.g., 0.3 and 0.5, it is possible, by using one, two or three of these systems, to attain doses of, e.g., 0.3, 0.5, 0.6, 0.8, 0.9, 1.0, 1.1, 1.3, 1.5, 1.6, 1.8, 2.0, 2.3, 2.5, and 3.0 unit-doses. With an increase in the number of available fractional unit-dose modules of differing fractional values and/or an increase in the number of systems that can be utilized, it is possible to achieve any target number of unit-doses. In this manner, it is possible to individualize the dose during long-term therapy based on the results from the short-term therapy period.

However, even if the short-term formulation and dosing-regimen matching is not optimal when compared to that expected with the long-term formulation and long-term delivery system, the use of a first, short-term formulation, whether recently or in the past, will nonetheless facilitate recognition of useful antiviral effects (in the case of hepatitis C) and the recognition of adverse effects that appear early during the course of therapy with an interferon. It will also help to prevent the premature selection of a dose or dose-rate with the long-term delivery system that is too low to be effective or too high to be safe and tolerated.

If the short-term formulation is delivered in such a manner that the delivery characteristics match very closely those of the long-term formulation and attendant long-term delivery system, then the total dose per day, per week or per month (or for any other convenient unit of time) found to be effective, safe, and tolerated using the short-term formulation, can be prepared for the long-term formulation. Those skilled in the art will recognize that this process of dose approximation will apply to chemically modified or unmodified, and glycosylated or nonglycosylated (or both) interferons or other interferon-like proteins that have interferon activity.

Method of Manufacturing

Another aspect of the invention is a method of manufacturing a delivery system for delivering a drug, such as omega-IFN, over time in a controlled manner. The method comprises preparing a long-term delivery device designed for delivery of a drug at a relatively constant rate over time, the rate being determined to be a standard dosage rate designed for a patient to receive a standard dosage amount over a unit of time to treat a disease state in the patient treatable over time by the drug, and preparing a plurality long-term delivery system designed for delivery of the drug at a relatively constant rate over time, which rate for each module is a fraction of the standard dosage rate. More than one unit dose or more than one fractional dose may be selected. Each system is suitable for presentation to a patient in need thereof alone or in combination with an identical system or a long-term formulation delivering the standard dosage rate, depending on the dosage rate or fractional dosage rate determined to be appropriate for the patient.

By way of specific example, a short-term formulation of omega interferon is administered to a patient with chronic HCV for one or two weeks. The weekly dose may range from 22.5 to 360 μg. The patient is evaluated for the presence of adverse symptoms, signs, or laboratory parameters. The level of HCV RNA is also measured. Laboratory parameters will usually include a measure of the white blood cell count, along with a white blood cell differential, so that the number of granulocytes can be determined. If HCV RNA levels have declined, preferably to undetectable levels, but the granulocyte count falls to less than 1000 cells/mm3, then the dose of omega interferon can be reduced by, for example, one-third or one-half. The HCV RNA level and granulocyte count are again monitored and when the granulocyte count returns to, for example, at least 2000 cells/mm$^3$ and the HCV RNA level is judged to be still satisfactorily reduced, then the long-term dosing system is injected or implanted without delay. The dose in the long-term delivery system is selected to suitably approximate the short-term dose previously shown to be effective and acceptably safe.

By way of another specific example, a short-term formulation of omega interferon is administered to a patient with chronic HCV for 4 months. There are no significant acute side effects and HCV RNA levels have been reduced by more than 99.99%. After 4 months of treatment, the patient becomes depressed. The depression is unresponsive to conventional oral antidepressants and the patient becomes suicidal. Omega interferon is temporarily stopped. The use of the short-term formulation facilitates a more rapid offset of action. The patient is hospitalized and receives electroshock therapy. Suicidal ideation ceases and depression remits. Omega interferon therapy is resumed at a lower dose using the short-term formulation. Depression does not reappear, HCV RNA levels are still reduced (more than 99%) and 4-6 months afterwards the long-term delivery system is selected to suitably approximate the new, reduced dose now shown to be effective and well tolerated.

By way of a third specific example, a patient with chronic HCV is treated for 6-12 months with a short-term dosing form of an alpha interferon (whether or not pegylated, with or without oral ribavirin). After one year of treatment with the alpha interferon regimen, HCV RNA levels have been reduced by approximately 80% but are still detectable. Treatment with the alpha interferon regimen is halted. 1-12 months later, omega interferon is administered for two weeks using a short-term dosing form, and suitable laboratory and clinical tests are conducted to demonstrate viral responsiveness to therapy in the absence of unacceptable acute side effects.

The system can be viewed then as a kit that can be used by the doctor or other provider of health care to individualize the dosage rate for a patient over time depending on the patient's characteristics such as age, gender, size, health condition, etc. The most commonly prescribed dose or dosage rate can be viewed as the median or "standard" or "unit" dosage. However, for a person who is physically of lower body mass than the median body mass for all patients, a the use of two delivery systems, each giving about 40% of the "unit" dosage rate, may be appropriate, i.e. a total of 80%, while a person with a body mass substantially higher than the median may require 140% of the unit dosage rate, e.g. a unit dose system plus a second system releasing at 40% of the unit dose rate.

The Kit

Still another aspect of this invention is a kit useful for delivery of a relatively constant amount of a drug thereof over time, wherein the amount of drug delivered to an individual patient within a population can be adjusted to the patient's individual needs for treatment. The kit comprises at least one long-term delivery formulation designed for delivery of a drug at a relatively constant rate over time, the rate being determined to be a unit rate as a standard dosage to treat a disease state in a patient in the population over time, and at least one long-term delivery system or device designed for delivery of the same drug at a relatively constant rate over time, which rate is a fraction of the standard dosage rate. Each formulation in the kit is suitable for presentation to a patient in need thereof alone as a standard dosage formulation or a fractional amount thereof.

The kit can also comprise a combination of two or more identical systems, depending on the dosage rate determined to be appropriate for the patient.

The kit can also comprise at least two or more long-term delivery device designed for delivery of the same drug at the same or different (yet relatively constant) rates over time, for which each rate is a fraction of the standard dosage rate, wherein each device in the kit is suitable for presentation to a patient in need thereof alone or in combination with an identical module or the other standard device, depending on the dosage rate determined to be appropriate for the patient.

The kit can also comprise a combination of a short-term formulation with a delivery device or system therefor and one or more identical or different long-term delivery systems containing the long-term formulation.

For example, different kits are shown in the table below:

| | | | | |
|---|---|---|---|---|
| Short-term dosing form (number of days) | none | 7 | 14 | 90 |
| Long-term dosing form #1 (units) | 0.4 | 1.0 | 1.0 | 1.0 |
| Long-term dosing form #2 (units) | 0.4 | none | 1.0 | 0.1 |
| Long-term dosing form #3 (units) | none | none | none | 0.1 |
| total long-term units | 0.8 | 1.0 | 2.0 | 1.2 |

The examples in the table are non-limiting, and those skilled in the art will recognize that other combinations are possible.

Both the method of manufacture and the kit aspects of the invention preferably will include a further refinement. This is the presence of written dosing instructions. The dosing instructions are for adjusting the rate of administration of the drug by employing one or a combination of devices to achieve the desired release rate of the drug for an individual patient depending on the patient's needs over time.

For example, in addition to the long-term dosing system(s) contained in the kit, with or without short-term dosing systems, the kit may also include written dosing material may describe the use of omega interferon, or other interferon, in an immunodiagnostic or immunotherapeutic protocol to determine the appropriate short-term and long-term dosing. Other factors to be considered in the protocol comprise the medical disorder to be treated and, in the case of viral hepatitis C, the patient or viral factors that may affect responsiveness to an interferon, e.g., viral subtype and viral load as well as characteristics of the patient comprising age, sex, weight, height, race or ethnicity, genetic profile comprising single nucleotide polymorphisms or haplotypes, the duration and severity of the medical disorder, the presence and severity of hepatic injury, concomitant illnesses, concomitant medications and the like.

For example, written material can be applied directly to a container (such as by the application of a label directly to a vial containing the interferon with or without carriers or excipients). Alternatively, a container-closure system holding the interferon can be placed into a second container, such as a box, and the written material, in the form of a packaging insert, can be placed in the second container together with the first container-closure system holding the interferon.

The written portion may describe indications for prescribing the drug, e.g., an interferon such as omega interferon, either as monotherapy or as part of combination therapy with one or more other interferons, with one or more non-interferons, or a combination or mixture of other drugs. Such indications would include an interferon-responsive disorder (for example, viral hepatitis C). The written material should further describe that the interferon or other interferon, as monotherapy or part of a combination therapy regimen, is useful for the treatment of, for example, viral hepatitis C.

In a preferred embodiment of this invention, the written material will describe omega interferon as the interferon to be used in treatment. In a most preferred embodiment, the written material will describe that omega interferon is used in the treatment of viral hepatitis, in particular viral hepatitis C and viral hepatitis B.

In other embodiments, the written material may describe that the interferon is of a recombinant form, manufactured in bacterial cells (and therefore usually nonglycosylated) or manufactured in mammalian cells (and therefore usually glycosylated). The written material will also describe whether the interferon is chemically unmodified or has been chemically modified by the addition of, for example, polyethylene glycol moieties of various lengths and at various sites of attachment to the interferon. The written material will also describe how to administer the long-term formulation or module.

Still further, it can be described in the written material that the appropriate dose to establish the initial safety, tolerability, and efficacy profile of the short-term formulation is provided by administering, on average, 1-210 μg per week of omega-IFN, and in a more preferred embodiment 9-60 μg per week. The written materials will describe the protocol to be followed to adjust the initial dose in response to observed events relevant to safety, tolerability, and efficacy of the interferon. The written materials will also reference one or more long-term delivery systems containing an interferon and the protocol for selecting the dose or dose-rate to be delivered by said long-term delivery system containing or used with the related long-term formulation.

The written material would preferably be provided in the form required by the regulatory agency with jurisdiction over the approval for marketing of such an interferon, such as the United States Food and Drug Administration, in the form of a package insert for a prescription drug. The written material would indicate that the interferon would be prescribed for use in patients having an interferon-responsive disorder. In a preferred embodiment, the written material would indicate that the interferon is omega interferon and that the interferon responsive-disorder is viral hepatitis, in particular viral hepatitis C. The written material would indicate that the interferon is useful as primary or secondary treatment or in combination with other treatments. It would further describe that while the interferon has an effect on the infected liver in patients with viral hepatitis C that the interferon also may reach other tissues where it may have no therapeutic effect.

Principal toxicities could also be described and could include, by way of example, headache, flu-like symptoms, pain, fever, asthenia, chills, infection, abdominal pain, chest pain, injection site reaction (as appropriate), malaise, hypersensitivity reaction, syncope, vasodilatation, hypotension, nausea, constipation, diarrhea, dyspepsia, anorexia, anemia, thrombocytopenia, leukopenia, other blood dyscrasias, myalgia, arthralgia, insomnia, dizziness, suicidal ideation, depression, impaired ability to concentrate mentally, amnesia, confusion, irritability, anxiety, nervousness, decreased libido, urticaria, alopecia, and others.

It may further be described in the written material that when symptoms such as fever, chills, or flu-like manifestations are observed that these can be treated with Tylenol®, antihistamines such as Benadryl®, and that hypotension may respond to the administration of fluids or pressor agents or, if the symptoms or signs are sufficiently severe, that the dose should be reduced or treatment terminated.

The written material may also describe that delivery of the formulation of the interferon intended for short-term administration is by injection, infusion, inhalation, oral or transdermal administration. The preferred embodiment is by injection or infusion and the most preferred is by injection. Warnings, precautions, and contraindications should be described.

Example of a Dosimetry Protocol

In treating a disease such as hepatitis C, antiviral effects from administration of an interferon may become obvious within hours or within a few days. Accordingly, in order to begin the assessment of the safety, tolerability, and effectiveness of the short-term formulation of the interferon, it is informative to utilize a short-term dosimetry protocol to assess antiviral effects. This protocol is a further elucidation of the invention.

At baseline (preferably within 1 hour prior to the initiation of dosing with the short-term formulation) and at, preferably, 8 and 14 days after dosing has begun, chemistry, hematology, and liver function testing are performed. Samples for hepatitis C viral ribonucleic acid levels (HCV RNA) testing are then obtained at baseline and again preferably at 2, 4, 7, 10, 14, 19 and 24 hours after dosing on Day 1 (the initial dose of interferon); at 5 and 10 hours after dosing on Day 2; and immediately prior to the daily omega interferon dose on Days 3, 4, 5, 6, 8, 10, 12 and 14 of dosing. Similar tests can then be performed, if required, at 2-4 weeks intervals while viral response and safety and tolerability are being assessed while the short-term formulation is being administered. Most preferably, this assessment is performed using omega interferon.

Responsiveness to treatment can be assessed by various parameters, ranging from
- a lack of detectable HCV RNA (viral load is below the lower limit of detectability for the assay being used) or
- a decrease in HCV RNA level to less than a preselected percentage of baseline viral load, e.g., 50% of pretreatment level,
- a decrease in a liver enzyme such as alanine amino transferase (ALT) to normal or to less than a preselected percentage of baseline viral load, e.g., 50% of pretreatment level or
- histopathological changes as assessed by liver biopsy.

Dosing at different levels and for variable periods of time may be necessary to establish an adequate safety, tolerability, and efficacy profile (i.e. maximize therapeutic response and minimizing adverse effects) for the short-term formulation and to enhance the predictive power of the information acquired during the use of the short-term formulation. The duration of such assessments could be as short as one day but preferably such assessments are made for at least one week, more preferably for two to four weeks, and most preferably for four to eight weeks.

Assessment of antiviral response or measurement of changes in liver function tests may necessary in order to select a dosage (i.e. dose-level or dose-rate level) intended for long term administration from a long-term delivery system. Very rapid assessment of antiviral effects in patients with hepatitis C can now be accomplished as described below. The invention is not limited by the particular viral pharmacodynamic model, doses, time or time intervals, or factors to be considered in the application of a particular model. Although assessment of antiviral response is preferable to occur within no more than days or a few weeks of initiating long-term therapy, the current invention encompasses the possibility that initial antiviral assessment may have occurred weeks, months, or possibly a year or more prior to the initiation of long-term treatment.

Description of Modeling of Viral Kinetics

To model the kinetics of hepatitis C viral kinetics during treatment with omega interferon, we have used a standard model of viral infection described by the differential equations:

$$dT/dt = s - dT - (1-\eta)\beta VT$$

$$dI/dt = (1-\eta)\beta VT - \delta I$$

$$dV/dt = (1-\epsilon)pI - cV$$

where the terms are defined as shown in the table below:

| | Definition of Terms |
|---|---|
| T | Number of target cells |
| t | Time |
| d | Rate constant for death of target cells |
| s | Rate of production of target cells |
| $\eta$ | Fractional reduction in de novo rate of infection of target cells |
| $\beta$ | Rate constant for de novo infection of target cells |
| V | Viral load |
| I | Number of productively infected cells |
| $\delta$ | Rate constant for death of infected cells |
| $\epsilon$ | Fractional reduction in production of virions by infected cells |
| p | Rate of production of virions by infected cell |
| c | Rate constant for clearance of virions |

If it is assumed that initially $\eta=0$ and that the number of productively infected cells remains relatively constant for the first two days of therapy, then the viral load (V) at time t, V(t), is $$V(t) = V_0[1 - \epsilon + \epsilon\exp(-c(t-t_0))]$$

The parameters $\epsilon$ and c can be estimated, among others, for each patient using nonlinear regression analysis to fit the above equation to the HCV RNA levels measured for the 48 hours after initiation of omega interferon dosing. Using those parameter values calculated for each patient and assuming the number of target cells remains relatively constant over the two weeks of therapy, nonlinear regression analysis can also be used to estimate the parameter $\delta$ for each patient using the equation $$V(t) = V_0\{A\exp[\lambda_1(t-t_0)] + (1-A)\exp[-\lambda_2(t-t_0)]\}$$

where $$\lambda_{1,2} = \frac{1}{2}\{(c+\delta) \pm [(c-\delta)^2 + 4(1-\epsilon)c\delta]^{1/2}\}$$

$$A = (\epsilon c - \lambda_2)/\lambda_1 - \lambda_2$$

Fitting these equations to the data obtained in clinical testing with two different doses of omega interferon in patients with alpha-interferon resistant hepatitis C, we have estimated the following values for the key parameters of antiviral effect, $\epsilon$ and C.

| | Mean Value | |
|---|---|---|
| Parameter | 15 ug/day (n = 7) | 30 ug/day (n = 4) |
| $\epsilon$ | .75 | .78 |
| c | 7.25 day$^{-1}$ | 3.10 day$^{-1}$ |

These findings indicate that, on average, there is a 75-78% reduction in virion production by infected cells and that the rate constant for virion clearance increases with increasing dose, i.e., that the time required for a given clearance level is decreasing.

The analysis of data from a clinical study of the type described in patients with viral hepatitis C can estimate the activity of several doses of interferon and the time-course and mechanism(s) of antiviral activity. The model parameter measuring initial antiviral activity is $\epsilon$ the fractional reduction in the production of virions by infected cells. For any group of patients treated at one dose level, it is possible to determine the group range, median, and mean (with 95% confidence interval by Normal approximation) for ε. The same group of patients can then be treated at a different dose level and the antiviral effects compared within and between patients. The data from this type of study can be used to guide the selection of dose(s) to be administered during long-term treatment.

It is possible to perform the multiple pairwise comparisons of ε calculated for the multiple dosing groups of patients. For each pair of groups it is possible to report the difference in mean ε (with 95% confidence interval by Normal approximation) and median ε (with 95% confidence intervals).

As an additional evaluation of possible antiviral activity, it is possible to examine the percent change in serum HCV RNA, alanine amino transferase (ALT) and aspartate amino transferase (AST) from baseline to the end of therapy for each patient, as well as the group medians and means (with 95% confidence intervals by Normal approximation).

The relationship baseline ALT levels and initial viral load to ε and relationship of baseline ALT and initial viral load to δ can be assessed using appropriate statistics. All changes in physical examinations, all adverse events and any significant changes in laboratory parameters can be assessed and compared, if need be, between different dosing groups or between different dose levels or dose rates for the same patient.

Such effects after administration of a short-term formulation can be determined over a short period of time measured in hours to days to longer periods of time, measured in days to weeks or, if necessary, even weeks to months before selecting the long-term dose or dose-rate and changing from administering the (first) short-term formulation to administering the (second) long-term formulation, whether a single formulation or a combination of modules.

In one embodiment, dosing with an interferon is performed at intervals ranging from 2 to 24 hours in order to establish a target steady state blood or tissue level. Dosing at this frequency may be maintained for 1 to 3 or more days after which dosing frequency may be reduced at the discretion of the health care provider.

The object of the administration of the short-term formulation is to determine a generally effective and generally safe and tolerated dose, i.e. to improve the therapeutic index. This object can be achieved by step-wise adjustments in the dose of interferon delivered with the short-term formulation. Dosing can be initiated at what is believed to be a low or even ineffective dose and escalated at regular or irregular intervals. Dosing escalation can continue until a poorly tolerated dose is reached or until a maximally effective dose is reached (based on antiviral effects and desirable changes in liver function tests). Then dosing can be stabilized or reduced moderately and then stabilized to test the effectiveness and tolerability of the chosen dose level or dose-rate. See FIG. 5 for a visual representation of this sequence of events.

The dose to be delivered with the long-term formulation can be adjusted to match the most generally effective and generally safe and tolerated dose as determined by use of the short-term formulation during the short-term formulation treatment period. To maximize the utility of the data from use of the short-term formulation, the dose, dose interval and dosing frequency of the short-term formulation is preferably adjusted to produce a drug delivery profile that matches as closely as possible that which is to be delivered by the long-term formulation.

The following examples of the present invention are provided to illustrate the invention in more detail. The examples are to be taken as illustrative only, without limiting the scope of the invention.

Example 1

Omega Interferon in a Short-Term Formulation Followed by Omega Interferon in a Long-Term Formulation Suitable for Use in an Implantable, Non-Erodible Drug Delivery Formulation Preparation and Administration of Omega Interferon in a Short-Term Formulation Omega interferon is produced by standard genetic engineering techniques in *E. coli* bacteria or in mammalian Chinese hamster ovary cells. Such techniques are further described for interferons generally in U.S. Pat. No. 4,727,138 and more specifically for omega interferon in U.S. Pat. No. 5,120,832 and U.S. Pat. No. 5,231,176. The interferon is then purified and used immediately or frozen and then subsequently thawed for use. The interferon may be lyophilized with appropriate stabilizers for subsequent reconstitution with water-for-injection or other suitable solvent or the interferon may be prepared for use initially as a liquid formulation.

For a lyophilized preparation of omega interferon 33 µg of omega interferon (measured by the amount of protein present) is prepared along with, by way of example, human serum albumin 25% (5 mg), potassium chloride (0.2 mg), potassium dihydrogen phosphate (0.2 mg), sodium chloride (8.0 mg). This lyophilized preparation is maintained at 2-8° C. and then reconstituted with 1 mL of sterile water-for-injection. As known to those skilled in the art, other formulations are possible.

For a liquid formulation of an interferon, the interferon is dissolved in 1 mL sterile water-for-injection which can also contain sodium chloride (7.5 mg), sodium phosphate dibasic (1.8 mg), sodium phosphate monobasic (1.3 mg), edetate disodium (0.1 mg), polysorbate 80 (0.1 mg), and m-cresol (1.5 mg) as a preservative, among other excipients known to those skilled in the art.

This short-term formulation is then administered by subcutaneous or intramuscular injection or by bolus intravenous injection or by infusion, preferably by subcutaneous injection.

A formulation for long-term use is dependent upon the long-term delivery formulation. For a non-erodible implant, a suitable formulation will be stable at the body temperature of warm-blooded animals for the duration of the dose contained by or within the system. It has been demonstrated that an interferon remains chemically stable and active in a perfluorocarbon solvent such as perfluorodecalin. Non-erodible implantable systems suitable for use in delivery of a long-term formulation are described in U.S. Pat. Nos. 4,976,966, 5,112,614, 5,660,847, 5,728,396, 5,985,305, 6,113,938, which are incorporated herein by reference.

After determination of a safe, tolerated and effective dose using the first, short-term formulation, preferably wherein the selection was made by replicating the pharmacokinetics of delivery of the long-term system using the short-term formulation and appropriately selected doses and dosing intervals, the long-term dose and dose-rate are selected. One skilled in the art will know that it is then necessary only to load the long-term delivery system with the predetermined total dose.

Alternatively, a generally safe and effective total dose per unit time is established for a population of animals with an interferon-responsive disease using the short-term formulation. The most preferred interferon is omega interferon. The most preferred interferon-responsive disease is viral hepatitis C. The unit of time may be conveniently selected from day, week, month, or quarter-year.

The preferred unit of time is chosen with regard to factors that comprise the maximal delivery period of the selected long-term delivery system, the most reliable delivery period for a selected long-term delivery formulation, the particular interferon, the stability of the interferon in the long-term formulation.

For the convenience of humans to be treated with the current invention, the preferred unit of time for the drug to be delivered over the long-term in the long-term formulation is either the month or quarter-year and the most preferred is the quarter-year. This gives the physician an opportunity to review progress in the patient and to continue long-term treatment as needed.

Unit Dose and Fractional Unit Modules

The total dose for the selected unit of time is then selected as the "unit-dosage" for the long-term delivery system. In the case of an implantable, non-erodible delivery system, the system may also be loaded with fractional unit doses. In the case of bio-erodible systems, either lesser volumes of the bio-erodible system are utilized or fractional amounts of the unit-dose are loaded into or onto the system.

In the case of viral hepatitis C, the preferred unit-dose per quarter-year is 300-8100 µg (i.e., about 23 to about 623 µg per week) of omega-IFN. A more preferred unit-dose per quarter-year is 300-5040 µg (i.e., about 23 to about 388 µg per week) and the most preferred unit-dose per quarter-year is 630-2520 µg (i.e., about 48 to about 194 µg per week).

Those skilled in the art will understand that with a unit-dose and, if desired, one or more fractional unit-dose module, the long-term dose can be individualized for an animal with an interferon-responsive disorder and to achieve a practical matching of the long-term dose with the dose determined from the previous use of the short-term formulation.

Those skilled in the art will recognize, however, that for practical purposes in the therapy of interferon-responsive disorders, a range of unit-doses will be safe, tolerated, and effective, thus minimizing the need for excessively numerous fractional unit-dose modules. Moreover, if the unit-dose is well chosen and based on data from a sufficiently large number of humans with interferon-responsive disorders, then it is possible to minimize further the need for a large number of long-term unit-dosage formulations or fractional unit-dose modules. Notwithstanding the foregoing, with knowledge of the results of the use of the short-term formulation, a unit-dose system (i.e. the long-term formulation) used with or without one or more fractional unit-dose modules provides great flexibility in the selection of dose, individualization of long-term dosing and optimization of long-term dosing.

Example 2

Omega Interferon in a Short-Term Formulation Followed by Omega Interferon in a Long-Term Formulation Suitable for Use in an Implantable or Injectable Erodible or Dispersible Drug Delivery System Omega interferon is prepared for short-term use as described in EXAMPLE 1.

Erodible or dispersible implantable or injectable drug delivery systems suitable for use in the long-term delivery of an interferon, including omega interferon, include such systems as described in U.S. Pat. No. 5,543,156, which is incorporated herein by reference, as well as in U.S. Pat. Nos. 5,529,914, 5,858,746, and 6,129,761, which are also incorporated herein by reference.

Those skilled in the arts will recognize that the current invention can be utilized to optimize or improve the long-term treatment of warm-blooded animals with any interferon-responsive condition and with any interferon or interferon-like molecule suitable for short-term formulation or suitable for long-term formulation with an appropriately chosen long-term delivery system, and whether employed as monotherapy or as part of a combination therapy regimen.

All articles, patents and other information cited herein are incorporated by reference for all purposes.

The subject matter claimed is:

1. A method of treating hepatitis C virus (HCV) infection in a subject in need of such treatment, wherein the HCV infection exhibits primary or secondary resistance to treatment with alpha interferon, comprising
administering a therapeutically effective amount of omega interferon protein to the subject, the administering selected from the group consisting of:
(i) is at a controlled rate over time and the therapeutically effective amount of omega interferon is an amount of omega interferon selected from the group consisting of between 48 and 194 micrograms per week, between 23 and 388 micrograms per week, and between 23 and 623 micrograms per week, and
(ii) is by injection and the therapeutically effective amount of omega interferon is an amount of omega interferon selected from the group consisting of between about 1 and about 210 micrograms per week and between about 22.5 and about 360 micrograms per week.

2. The method of claim 1, wherein the therapeutically effective amount of omega interferon is administered by injection.

3. The method of claim 2, wherein the therapeutically effective amount of omega interferon is administered by one or more daily injections.

4. The method of claim 2, wherein the therapeutically effective amount of omega interferon is administered by one or more injections given at selected dosing intervals.

5. The method of claim 4, wherein the dosing interval comprises three injections per week.

6. The method of claim 2, wherein the method of injection is selected from the group consisting of subcutaneous injection, intramuscular injection, and bolus intravenous injection.

7. The method of claim 6, wherein the omega interferon is administered by subcutaneous injection.

8. The method of claim 1, wherein the omega interferon is administered by infusion.

9. The method of claim 8, wherein the method of infusion is chronic intravascular infusion.

10. The method of claim 1, wherein the omega interferon is administered at a controlled rate over time.

11. The method of claim 10, wherein a device is used to administer the omega interferon.

12. The method of claim 11, wherein the device comprises a pump.

13. The method of claim 12, wherein the device is either implanted in or external to the subject.

14. The method of claim 13, wherein the device is implanted.

15. The method of claim 14, wherein the device comprises an osmotic pump.

16. The method of claim 10, wherein two or more implantable devices are used to administer the omega interferon.

17. The method of claim 1, wherein the therapeutically effective amount of injected omega interferon is between about 1 and about 210 micrograms per week.

18. The method of claim 1, wherein the therapeutically effective amount of injected omega interferon is between about 22.5 and about 360 micrograms per week.

19. The method of claim 1, wherein the therapeutically effective amount of omega interferon administered at a controlled rate over time is between 23 and 623 micrograms per week.

20. The method of claim 1, wherein the omega interferon is a recombinant omega interferon.

21. The method of claim 1, wherein the treatment with alpha interferon further comprises treatment with ribavirin.

22. A method of treating hepatitis C virus (HCV) infection in a subject in need of such treatment, wherein the HCV infection exhibits primary or secondary resistance to treatment with alpha interferon, comprising administering a therapeutically effective amount of omega interferon protein to the subject, the administering selected from the group consisting of:

(i) is at a controlled rate over time and the therapeutically effective amount of omega interferon is an amount of omega interferon selected from the group consisting of between 48 and 194 micrograms per week, between 23 and 388 micrograms per week, and between 23 and 623 micrograms per week, and (ii) is by injection and the therapeutically effective amount of omega interferon is an amount of omega interferon selected from the group consisting of between about 1 and about 210 micrograms per week and between about 22.5 and about 360 micrograms per week;

wherein the therapeutically effective amount of omega interferon protein is administered over at least about one month.

* * * * *

UNITED STATES PATENT AND TRADEMARK OFFICE
CERTIFICATE OF CORRECTION

PATENT NO.       : 7,727,519 B2
APPLICATION NO.  : 10/982532
DATED            : June 1, 2010
INVENTOR(S)      : Stanford Mark Moran It is certified that error appears in the above-identified patent and that said Letters Patent is hereby corrected as shown below:

Title page, item (75) inventor: Delete "Mark Stanford", insert -- Stanford Mark --

Column 2, line 23: Delete "~", insert -- ≈ --

Column 10, line 30: Delete "ρ", insert -- τ --

Signed and Sealed this

Seventh Day of September, 2010

David J. Kappos
*Director of the United States Patent and Trademark Office*